US007842787B2

(12) United States Patent
Popplewell et al.

(10) Patent No.: US 7,842,787 B2
(45) Date of Patent: Nov. 30, 2010

(54) BIOLOGICAL PRODUCTS

(75) Inventors: Andrew George Popplewell, Berkshire (GB); Simon Peter Tickle, Berkshire (GB); Karen Zinkewich-Peotti, Berkshire (GB); Robert Kendall Morrison, Berkshire (GB)

(73) Assignee: UCB Pharma S.A., Brussels (BE)

( * ) Notice: Subject to any disclaimer, the term of this patent is extended or adjusted under 35 U.S.C. 154(b) by 485 days.

(21) Appl. No.: 11/928,880

(22) Filed: Oct. 30, 2007

(65) Prior Publication Data

US 2009/0269840 A1   Oct. 29, 2009

Related U.S. Application Data

(62) Division of application No. 10/492,228, filed as application No. PCT/GB02/04619 on Oct. 10, 2002, now Pat. No. 7,452,976.

(30) Foreign Application Priority Data

Oct. 10, 2001   (GB)   .................... 0124317.9

(51) Int. Cl.
*C07K 16/00* (2006.01)
(52) U.S. Cl. .................... 530/387.1; 435/325
(58) Field of Classification Search ........... None
See application file for complete search history.

(56) References Cited

U.S. PATENT DOCUMENTS 6,133,426 A   10/2000   Gonzalez et al.

FOREIGN PATENT DOCUMENTS

| EP | 0 239 400 A2 | 9/1987 |
|---|---|---|
| EP | 1 086 705 A1 | 3/2001 |
| WO | WO 89/01476 | 2/1989 |
| WO | WO 90/07861 | 7/1990 |
| WO | WO 90/09195 | 8/1990 |
| WO | WO 91/09967 | 7/1991 |
| WO | WO 92/01059 | 1/1992 |
| WO | WO 92/22583 | 12/1992 |
| WO | WO 93/06231 | 4/1993 |
| WO | WO 94/11499 | 5/1994 |
| WO | WO 98/11223 | 3/1998 |
| WO | WO 98/20734 | 5/1998 |
| WO | WO 98/58053 | 12/1998 |
| WO | WO 99/64460 | 12/1999 |
| WO | WO 00/44777 | 8/2000 |

OTHER PUBLICATIONS

Lu et al. (JBC, vol. 275(19), pp. 14321-14330, May 2000).*
Ausubel (Ed.), Current Protocols in Molecular Biology, Wiley, NY (1999).
Brekken, R.A., et al., "Selective Inhibition of Vascular Endothelial Growth Factor (VEGF) Receptor 2 (DKR/Flk-1) Activity by a Monoclonal Anti-VEGF Antibody Blocks Tumor Growth in Mice," *Cancer Research*, 60:5117-5124, (Sep. 2000).
Brown, L.F., et al., "Expression of Vascular Permeability Factor (Vascular Endothelial Growth Factor) and Its Receptors in Adenocarcinomas of the Gastrointestinal Tract," *Cancer Research*, 53:4727-4735, (Oct. 1993).
Brown, L.F., et al., "Expression of Vascular Permeability Factor (Vascular Endothelial Growth Factor) and its Receptors in Breast Cancer," *Human Pathol.*, 26:86-91, (1995).
Chapman, A.P., "Therapeutic antibody fragments with prolonged in vivo half-lives," *Nature Biotechnology*, 17:780-783, (Aug. 1999).
Cheng, S.Y., et al., "Suppression of glioblastoma angiogenicity and tumorigenicity by inhibition of endogenous expression of vascular endothelial growth factor," *Proc. Natl. Acad. Sci., USA*, 93:8502-8507, (Aug. 1996).
Crameri, A., et al., "DNA shuffling of a family of genes from diverse species accelerates directed evolution," *Nature*, 391(6664):288-291, (Jan. 1988).
Cunningham, S.A., et al., "KDR activation is crucial for VEGF165-mediated Ca2+ mobilization in human umbilical vein endothelial cells," *Am. J. Physiol.*, 276(Cell Physiol., 45):C176-C181, (1999).
Deckert, P.M., et al., "Pharmacokinetics and Microdistribution of Polyethylene Glycol-Modified Humanized A33 Antibody Targeting Colon Cancer Xenografts," *Int. J. Cancer*, 87(3):382-390, (2000).
Dvorak, H.F., et al., "Vascular Permeability Factor/Vascular Endothelial Growth Factor and the Significance of Microvascular Hyperpermeability in Angiogeneis," *Curr. Topics Microbiol. Immunol.*, 237:97-132, (1999).
Feinstein et al., "Immunoglobulin flexibility in complement activation," *Immunology Today*, 7(6):169-174. (1986).
Flanagan, J.G. and Rabbitts, T.H., "Arrangement of human immunoglobulin heavy chain constant region genes implies evolutionary duplication of a segment containing γ, ε and α genes," *Nature*, 300(5894):709-713, (Dec. 1982).
Folkman, J. and Klagsbrun, M., "Angiogenic Factors," *Science*, 235:442-447, (Jan. 1987).
Gerber, H.P., et al., "Vascular Endothelial Growth Factor Regulates Endothelial Cell Survival through the Phosphatidylinositol 3'-Kinase/Akt Signal Transduction Pathway," *J. Biol. Chem.*, 273(46):30336-30343, (Nov. 1998).
Goldman, C.K., et al., "Paracrine expression of a native soluble vascular endothelial growth factor receptor inhibits tumor growth, metastasis, and mortality rate," *Proc. Natl. Acad. Sci., USA*, 95:8795-8800, (Jul. 1998).
Hicklin, D.J., et al., "Monoclonal antibody strategies to block angiogenesis," *Drug Discovery Today*, 6(10):517-528, (2001).

(Continued)

*Primary Examiner*—Larry R. Helms
*Assistant Examiner*—Meera Natarajan
(74) *Attorney, Agent, or Firm*—Cozen O'Connor

(57) ABSTRACT

There are disclosed antibody molecules containing at least on CDR derived from a mouse monoclonal antibody having specificity for human KDR. There is also disclosed a CDR grafted antibody wherein at least one of the CDRs is a hybrid CDR. Further disclosed are DNA sequences encoding the chains of the antibody molecules, vectors, transformed host cells and uses of the antibody molecules in the treatment of diseases in which VEGF and/or KDR are implicated.

11 Claims, 24 Drawing Sheets

OTHER PUBLICATIONS

Hieter, P.A., et al., "Cloned Human and Mouse Kappa Immunoglobulin Constant and J Region Genes Conserve Homology in Functional Segments," *Cell,* 22(Part 1):197-207, (Nov. 1980).

Hiratsuka, S., et al., "FLT-1 lacking the tyrosine kinase domain is sufficient for normal development and angiogenesis in mice," *Proc. Natl. Acad. Sci., USA,* 95:9349-9354, (Aug. 1998).

Humphreys et al., F(ab')₂ molecules made from *Escherichia coli* produced FAB' with hinge sequences conferring increased serum survival in an animal model, *Journal of Immunological Methods,* 217:1-10 (Mar. 1998).

Hurwitz, E., et al., "Inhibition of tumor growth by poly(ethylene glycol) derivatives of anti-ErbB2 antibodies," *Cancer Immunol. Immunother.,* 49(4-5):226-234, (2000).

Kabat, et al., "In Sequences of Proteins of Immunological Interest," U.S. Department of Health and Human Services, NIH, USA, (1987).

Keyt, B.A., et al., "Identification of Vascular Endothelial Growth Factor Determinants for Binding KDR and FLT-1 Receptors," *J. Biol. Chem.,* 271(10):5638-5646, (Mar. 1996).

Kim, K.J., et al., "Inhibition of vascular endothelial growth factor-induced angiogenesis suppresses tumour growth in vivo," *Nature,* 362:841-844, (Apr. 1993).

King et al., "Improved Tumor Targeting with Chemically Corss-Linked Recombinant Antibody Fragments," *Cancer Res.,* 54:6176-6185 (Dec. 1994).

Koukourakis, M.I., et al., "Vascular Endothelial Growth Factor/KDR Activated Microvessel Density versus CD31 Standard Microvessel Density in Non-Small Cell Lung Cancer," *Cancer Research,* 60:3088-3095, (Jun. 2000).

Larrivée, B. and Karsan, A., "Signaling pathways induced by vascular endothelial growth factor (Review)," *Intl. J. Molecular Medicine,* 5:447-456, (2000).

Low, N.M., et al., "Mimicking Somatic Hypermutation: Affinity Maturation of Antibodies Displayed on Bacteriophage Using a Bacterial Mutator Strain," *J. Mol. Biol.,* 260:359-368, (1996).

Marks, J.D., "By-Passing Immunization: Building High Affinity Human Antibodies by Chain Shuffling," *Bio/Technology,* 10:779-783, (Jul. 1992).

Millauer, B., et. al., "Glioblastoma growth inhibited in vivo by a dominant-negative Flk-1 mutant," *Nature,* 367:576-579, (Feb. 1994).

Patten, P.A., et al., "Applications of DNA shuffling to pharmaceuticals and vaccines," *Current Opinion in Biotechnology,* 87:724-733, (1997).

Riechmann, L., et al., "Reshaping human antibodies for therapy," *Nature,* 332:323-327, (Mar. 1988).

Shibuya, M., et al., "Nucleotide sequence and expression of a novel human receptor-type tyrosine kinase gene (flt) closely related to the fms family," *Oncogene,* 5:519-524, (1990).

Takahashi, Y., et al., "Expression of Vascular Endothelial Growth Factor and Its Receptor, KDR, Correlates with Vascularity, Metastasis, and Proliferation of Human Colon Cancer," *Cancer Research,* 55:3964-3968, (Sep. 1995).

Terman, B.I., et al., "Identification of a new endothelial cell growth factor receptor tyrosine kinase," *Oncogene,* 6:1677-1683, (1991).

Thompson, J., et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," *J. Mol. Biol.,* 256:77-88, (1996).

Vaughan, T., et al., "Human antibodies by design," *Nature Biotechnology,* 16:535-539, (Jun. 1998).

Verhoeyen et al., "Reshaping human antibodies: grafting an antilysozyme activity," *Science,* 239:1534-1536 (1988).

Wada K.N., et al., "Codon usage tabulated from the GenBank genetic sequence data," *Nucleic Acids Research,* 19(Supplement):1981-1986, (1991).

Waltenberger, J., et al., "Different Signal Transduction Properties of KDR and Flt1, Two Receptors for Vascular Endothelial Growth Factor," *J. Biol. Chem.,* 269(43):26988-26995, (Oct. 1994).

Witte, L., et al., "Monoclonal antibodies targeting the VEGF receptor-2 (Flk1/KDR) as an anti-angiogenic therapeutic strategy," *Cancer and Metastasis Reviews,* 17:155-161, (1998).

Wu, T.T. and Kabat, E.A., "An Analysis of the Sequences of the Variable Regions of Bence Jones Proteins and Myeloma Light Chains and Their Implications for Antibody Complementarity," *J. Exp. Med.,* 132:211-250, (1970).

Yang, W.P., et al., "CDR Walking Mutagenesis for the Affinity Maturation of a Potent Human Anti-HIV-1 Antibody into the Picomolar Range," *J. Mol. Biol.,* 254:392-403, (1995).

Zhu, Z., et al., "Inhibition of vascular endothelial growth factor induced mitogenesis of human endothelial cells by a chimeric anti-kinase insert domain-containing receptor antibody," *Cancer Letters,* 136(2):203-213, (1999).

PCT International Search Report dated Jan. 9, 2004 for International Application No. PCT/GB02/04619, International Filing Date: Oct. 10, 2002.

\* cited by examiner

Figure 1: Sequence of CDRs of VR165

Heavy Chain

| | | |
|---|---|---|
| H1 | SYGMS | (SEQ. ID. NO. 1) |
| H2 | TITSGGSYTYYPDTVKG | (SEQ. ID. NO. 2) |
| H3 | IGEDALDY | (SEQ. ID. NO. 3) |

Light Chain

| | | |
|---|---|---|
| L1 | RASQDIAGSLN | (SEQ. ID. NO. 4) |
| L2 | ATSSLDS | (SEQ. ID. NO. 5) |
| L3 | LQYGSFPPT | (SEQ. ID. NO. 6) |

Figure 2: Protein sequence of mouse monoclonal antibody VR165 variable domains

Heavy Chain (SEQ. ID. NO. 7)

VR165    EVQLVESGGDLVKPGGSLKLSCAASGFTFSSYGMSWVRQTPDKRLQWVATITSGGSYTYYPDTVKG

VR165    RFTISRDNAENTLYLQMSSLKSEDTAMYYCVRIGEDALDYWGQGTSVTVSS

Light Chain (SEQ. ID. NO. 8)

VR165    DIQMTQSPSSLSASLGERVSLTCRASQDIAGSLNWLRQEPDGTIKRLIYATSSLDS

VR165    GVPKRFSGSRSGSDYSLTISSLESEDFVDYYCLQYGSFPPTFGGGSKLEIKR

Comparison of VR165 V-region to Chosen framework V-regions

Seq. Id. No. 9: VH3-7 GL V-region

```
VH3-7 GL    EVQLVESGGGLVQPGGSLRLSCAASGFTFSSYWMSWVRQAPGKGLEWVANIKQDGSEKYYVDSVKG
              | |        |           |              | | | |
VR165       EVQLVESGGDLVKPGGSLKLSCAASGFTFSSYGMSWVRQTPDKRLQWVATITSGGSYTYYPDTVKG

VH3-7 GL    RFTISRDNAKNSLYLQMNSLRAEDTAVYYCAR          WGQGTLVTVSS
              | |      | |    ||    |    |                |
VR165       RFTISRDNAENTLYLQMSSLKSEDTAMYYCVRIGEDALDYWGQGTSVTVSS
```

Seq. Id. No.10: A30 GL V-region

```
A30 GL      DIQMTQSPSSLSASVGDRVTITCRASQGIRNDLGWYQQKPGKAPKRLIYAASSLQS
                        | |   ||                || |  ||||
VR165       DIQMTQSPSSLSASLGERVSLTCRASQDIAGSLNWLRQEPDGTIKRLIYATSSLDS

A30 GL      GVPSRFSGSGSGTEFTLTISSLQPEDFATYYCLQHNSYP   FGQGTKVEIKR
              |    |   ||||       ||    ||     ||         | | |
VR165       GVPKRFSGSRSGSDYSLTISSLESEDFVDYYCLQYGSFPPTFGGGSKLEIKR
```

FIG. 3

Figure 4: Light Chain, including signal sequences

```
(Seq. Id. No. 13)   ATG AAA AAG ACA GCT ATC GCA ATT GCA
                    TAC TTT TTC TGT CGA TAG CGT TAA CGT (Seq. Id. No. 11)    M   K   K   T   A   I   A   I   A>

(Seq. Id. No. 13)   GTG GCC TTG GCT GGT TTC GCT ACC GTA GCG CAA GCT GAT ATC CAG ATG ACC CAG AGT
                    CAC CGG AAC CGA CCA AAG CGA TGG CAT CGC GTT CGA CTA TAG GTC TAC TGG GTC TCA (Seq. Id. No. 11)    V   A   L   A   G   F   A   T   V   A   Q   A   D   I   Q   M   T   Q   S>

(Seq. Id. No. 13)   CCA AGC AGT CTC TCC GCC AGC GTA GGC GAT CGT GTG ACT ATT ACC TGT CGT GCC AGT
                    GGT TCG TCA GAG AGG CGG TCG CAT CCG CTA GCA CAC TGA TAA TGG ACA GCA CGG TCA (Seq. Id. No. 11)    P   S   S   L   S   A   S   V   G   D   R   V   T   I   T   C   R   A   S>

(Seq. Id. No. 13)   CAG GAC ATC GCG GGT AGC CTG AAC TGG TTG CAG CAA AAA CCG GGC AAA GCC ATC AAG
                    GTC CTG TAG CGC CCA TCG GAC TTG ACC AAC GTC GTT TTT GGC CCG TTT CGG TAG TTC (Seq. Id. No. 11)    Q   D   I   A   G   S   L   N   W   L   Q   Q   K   P   G   K   A   I   K>

(Seq. Id. No. 13)   CGC CTC ATC TAT GCG ACG TCC AGC CTG GAT AGC GGT GTG CCA AAA CGT TTC AGT GGC
                    GCG GAG TAG ATA CGC TGC AGG TCG GAC CTA TCG CCA CAC GGT TTT GCA AAG TCA CCG
(Seq. Id. No. 11)    R   L   I   Y   A   T   S   S   L   D   S   G   V   P   K   R   F   S   G>

(Seq. Id. No. 13)   AGT CGC AGC GGT TCT GAC TAT ACC CTC ACA ATT TCG TCT CTC CAG CCG GAA GAT TTC
                    TCA GCG TCG CCA AGA CTG ATA TGG GAG TGT TAA AGC AGA GAG GTC GGC CTT CTA AAG (Seq. Id. No. 11)    S   R   S   G   S   D   Y   T   L   T   I   S   S   L   Q   P   E   D   F>

(Seq. Id. No. 13)   GCC ACT TAC TAT TGT CTG CAA TAT GGC AGC TTC CCT CCG ACC TTC GGT CAG GGC ACT
                    CGG TGA ATG ATA ACA GAC GTT ATA CCG TCG AAG GGA GGC TGG AAG CCA GTC CCG TGA (Seq. Id. No. 11)    A   T   Y   Y   C   L   Q   Y   G   S   F   P   P   T   F   G   Q   G   T>

(Seq. Id. No. 13)   AAA GTA GAA ATC AAA CGT ACG GTA GCG GCC CCA TCT GTC TTC ATC TTC CCG CCA TCT
                    TTT CAT CTT TAG TTT GCA TGC CAT CGC CGG GGT AGA CAG AAG TAG AAG GGC GGT AGA (Seq. Id. No. 11)    K   V   E   I   K   R   T   V   A   A   P   S   V   F   I   F   P   P   S>

(Seq. Id. No. 13)   GAT GAG CAG TTG AAA TCT GGA ACT GCC TCT GTT GTG TGC CTG CTG AAT AAC TTC TAT
                    CTA CTC GTC AAC TTT AGA CCT TGA CGG AGA CAA CAC ACG GAC GAC TTA TTG AAG ATA (Seq. Id. No. 11)    D   E   Q   L   K   S   G   T   A   S   V   V   C   L   L   N   N   F   Y>

(Seq. Id. No. 13)   CCC AGA GAG GCC AAA GTA CAG TGG AAG GTG GAT AAC GCC CTC CAA TCG GGT AAC TCC
                    GGG TCT CTC CGG TTT CAT GTC ACC TTC CAC CTA TTG CGG GAG GTT AGC CCA TTG AGG (Seq. Id. No. 11)    P   R   E   A   K   V   Q   W   K   V   D   N   A   L   Q   S   G   N   S>

(Seq. Id. No. 13)   CAG GAG AGT GTC ACA GAG CAG GAC AGC AAG GAC AGC ACC TAC AGC CTC AGC AGC ACC
                    GTC CTC TCA CAG TGT CTC GTC CTG TCG TTC CTG TCG TGG ATG TCG GAG TCG TCG TGG (Seq. Id. No. 11)    Q   E   S   V   T   E   Q   D   S   K   D   S   T   Y   S   L   S   S   T>

(Seq. Id. No. 13)   CTG ACG CTG AGC AAA GCA GAC TAC GAG AAA CAC AAA GTC TAC GCC TGC GAA GTC ACC
                    GAC TGC GAC TCG TTT CGT CTG ATG CTC TTT GTG TTT CAG ATG CGG ACG CTT CAG TGG (Seq. Id. No. 11)    L   T   L   S   K   A   D   Y   E   K   H   K   V   Y   A   C   E   V   T>

(Seq. Id. No. 13)   CAT CAG GGC CTG AGC TCA CCA GTA ACA AAA AGT TTT AAT AGA GGG GAG TGT TAA
                    GTA GTC CCG GAC TCG AGT GGT CAT TGT TTT TCA AAA TTA TCT CCC CTC ACA ATT (Seq. Id. No. 11)    H   Q   G   L   S   S   P   V   T   K   S   F   N   R   G   E   C   *>
```

Figure 5: Heavy Chain, including signal sequences

```
(Seq. Id. No. 14)   ATG AAG AAG ACT GCT ATA GCA ATT GCA GTG GCG CTA GCT GGT TTC GCC ACC GTG GCG CAA
                    TAC TTC TTC TGA CGA TAT CGT TAA CGT CAC CGC GAT CGA CCA AAG CGG TGG CAC CGC GTT
(Seq. Id. No. 12)    M   K   K   T   A   I   A   I   A   V   A   L   A   G   F   A   T   V   A   Q>

(Seq. Id. No. 14)   GCT GAG GTT CAG CTG GTC GAG TCT GGA GGC GGG CTT GTC CAG CCT GGA GGG AGC CTG
                    CGA CTC CAA GTC GAC CAG CTC AGA CCT CCG CCC GAA CAG GTC GGA CCT CCC TCG GAC
(Seq. Id. No. 12)    A   E   V   Q   L   V   E   S   G   G   G   L   V   Q   P   G   G   S   L>

(Seq. Id. No. 14)   CGT CTC TCT TGT GCA GCA AGC GGC TTC ACC TTT TCC TCT TAC GGT ATG TCC TGG GTG
                    GCA GAG AGA ACA CGT CGT TCG CCG AAG TGG AAA AGG AGA ATG CCA TAC AGG ACC CAC
(Seq. Id. No. 12)    R   L   S   C   A   A   S   G   F   T   F   S   S   Y   G   M   S   W   V>

(Seq. Id. No. 14)   CGG CAG GCA CCT GGG AAG GGC CTG GAG TGG GTG GCA ACC ATT ACG TCC GGA GGC AGC
                    GCC GTC CGT GGA CCC TTC CCG GAC CTC ACC CAC CGT TGG TAA TGC AGG CCT CCG TCG
(Seq. Id. No. 12)    R   Q   A   P   G   K   G   L   E   W   V   A   T   I   T   S   G   G   S>

(Seq. Id. No. 14)   TAT ACA TAC TAC GTG GAC AGC GTC AAG GGC CGT TTC ACC ATT TCC CGG GAC AAT GCA
                    ATA TGT ATG ATG CAC CTG TCG CAG TTC CCG GCA AAG TGG TAA AGG GCC CTG TTA CGT
(Seq. Id. No. 12)    Y   T   Y   Y   V   D   S   V   K   G   R   F   T   I   S   R   D   N   A>

(Seq. Id. No. 14)   AAG AAT ACC CTT TAC CTC CAG ATG AAC TCT CTC CGC GCA GAG GAC ACA GCA GTC TAT
                    TTC TTA TGG GAA ATG GAG GTC TAC TTG AGA GAG GCG CGT CTC CTG TGT CGT CAG ATA
(Seq. Id. No. 12)    K   N   T   L   Y   L   Q   M   N   S   L   R   A   E   D   T   A   V   Y>

(Seq. Id. No. 14)   TAC TGT GTA CGG ATC GGC GAA GAC GCG TTG GAC TAC TGG GGA CAG GGG ACC CTT GTG
                    ATG ACA CAT GCC TAG CCG CTT CTG CGC AAC CTG ATG ACC CCT GTC CCC TGG GAA CAC
(Seq. Id. No. 12)    Y   C   V   R   I   G   E   D   A   L   D   Y   W   G   Q   G   T   L   V>

(Seq. Id. No. 14)   ACA GTC TCC TCT GCT TCT ACA AAG GGC CCA TCG GTC TTC CCC CTG GCA CCC TCC TCC
                    TGT CAG AGG AGA CGA AGA TGT TTC CCG GGT AGC CAG AAG GGG GAC CGT GGG AGG AGG
(Seq. Id. No. 12)    T   V   S   S   A   S   T   K   G   P   S   V   F   P   L   A   P   S   S>

(Seq. Id. No. 14)   AAG AGC ACC TCT GGG GGC ACA GCG GCC CTG GGC TGC CTG GTC AAG GAC TAC TTC CCC
                    TTC TCG TGG AGA CCC CCG TGT CGC CGG GAC CCG ACG GAC CAG TTC CTG ATG AAG GGG
(Seq. Id. No. 12)    K   S   T   S   G   G   T   A   A   L   G   C   L   V   K   D   Y   F   P>

(Seq. Id. No. 14)   GAA CCG GTG ACG GTG TCG TGG AAC TCA GGC GCC CTG ACC AGC GGC GTG CAC ACC TTC
                    CTT GGC CAC TGC CAC AGC ACC TTG AGT CCG CGG GAC TGG TCG CCG CAC GTG TGG AAG
(Seq. Id. No. 12)    E   P   V   T   V   S   W   N   S   G   A   L   T   S   G   V   H   T   F>

(Seq. Id. No. 14)   CCG GCT GTC CTA CAG TCC TCA GGA CTC TAC TCC CTC AGC AGC GTG GTG ACC GTG CCC
                    GGC CGA CAG GAT GTC AGG AGT CCT GAG ATG AGG GAG TCG TCG CAC CAC TGG CAC GGG
(Seq. Id. No. 12)    P   A   V   L   Q   S   S   G   L   Y   S   L   S   S   V   V   T   V   P>

(Seq. Id. No. 14)   TCC AGC AGC TTG GGC ACC CAG ACC TAC ATC TGC AAC GTG AAT CAC AAG CCC AGC AAC
                    AGG TCG TCG AAC CCG TGG GTC TGG ATG TAG ACG TTG CAC TTA GTG TTC GGG TCG TTG
(Seq. Id. No. 12)    S   S   S   L   G   T   Q   T   Y   I   C   N   V   N   H   K   P   S   N>

(Seq. Id. No. 14)   ACC AAG GTC GAC AAG AAA GTT GAG CCC AAA TCT TGT GAC AAA ACT CAC ACA TGC GCC
                    TGG TTC CAG CTG TTC TTT CAA CTC GGG TTT AGA ACA CTG TTT TGA GTG TGT ACG CGG
(Seq. Id. No. 12)    T   K   V   D   K   K   V   E   P   K   S   C   D   K   T   H   T   C   A>

(Seq. Id. No. 14)   GCG TGA
                    CGC ACT
(Seq. Id. No. 12)    A   *>
```

Figure 7:

gH3  (SEQ ID NO: 15)

EVQLVESGGGLVQPGGSLRLSCAASGFTFSSYGMSWVRQAPGKGLEWVATIT
SGGSYTYYVDSVKGRFTISRDNAKNTLYLQMNSLRAEDTAVYYCVRIGEDAL
DYWGQGTLVTVSS gL3  (SEQ ID NO: 16)

DIQMTQSPSSLSASVGDRVTITCRASQDIAGSLNWLQQKPGKAIKRLIYATSSL
DSGVPKRFSGSRSGSDYTLTISSLQPEDFATYYCLQYGSFPPTFGQGTKVEIKR pTTOD(CDP791)

Protein sequence of the designed VH and VL grafts

Heavy Chain (Seq.Id.No. 17)

```
gH1        EVQLVESGGGLVQPGGSLRLSCAASGFTFSSYGMSWVRQAPGKGLEWVATITSGGSYTYYPDTVKG
gH1        RFTISRDNAKNSLYLQMNSLRAEDTAVYYCARIGEDALDYWGQGTLVTVSS
```

(Seq.Id.No. 18)

```
gH2        EVQLVESGGGLVQPGGSLRLSCAASGFTFSSYGMSWVRQAPGKGLEWVATITSGGSYTYYPDTVKG
gH2        RFTISRDNAKNTLYLQMNSLRAEDTAVYYCVRIGEDALDYWGQGTLVTVSS
```

(Seq.Id.No. 19)

```
gH3        EVQLVESGGGLVQPGGSLRLSCAASGFTFSSYGMSWVRQAPGKGLEWVATITSGGSYTYYVDSVKG
gH3        RFTISRDNAKNTLYLQMNSLRAEDTAVYYCVRIGEDALDYWGQGTLVTVSS
```

Light Chain (Seq.Id.No. 20)

```
gL1        DIQMTQSPSSLSASVGDRVTITCRASQDIAGSLNWYQQKPGKAPKRLIYATSSLDS
gL1        GVPSRFSGSGSGTEFTLTISSLQPEDFATYYCLQYGSFPPTFGQGTKVEIKR
```

(Seq.Id.No. 21)

```
gL2        DIQMTQSPSSLSASVGDRVTITCRASQDIAGSLNWYQQKPGKAPKRLIYATSSLDS
gL2        GVPKRFSGSRSGSDYTLTISSLQPEDFATYYCLQYGSFPPTFGQGTKVEIKR
```

(Seq.Id.No. 22)

```
gL3        DIQMTQSPSSLSASVGDRVTITCRASQDIAGSLNWLQQKPGKAIKRLIYATSSLDS
gL3        GVPKRFSGSRSGSDYTLTISSLQPEDFATYYCLQYGSFPPTFGQGTKVEIKR
```

Fig. 9

Figure 10: Gene design
gH1 sequence  (SEQ ID NO:23)

```
           HindIII      20              30              40              50              60
         GAATAAAAGC TTGCCGCCAC C ATG AAG ATG TGG TTA AAC TGG GTT TTC CTT GCC CTC ATT
         CTTATTTTCG AACGGCGGTG G TAC TTC TAC ACC AAT TTG ACC CAA AAG GAA CGG GAG TAA
                                  M   K   M   W   L   N   W   V   F   L   A   L   I>

70              80     PvuII    100             110
         TTA AAA GGT GTC CAG TGT GAG GTG CAG CTG GTC GAG TCT GGA GGC GGG CTT GTC CAG
         AAT TTT CCA CAG GTC ACA CTC CAC GTC GAC CAG CTC AGA CCT CCG CCC GAA CAG GTC
         L   K   G   V   Q   C   E   V   Q   L   V   E   S   G   G   G   L   V   Q>

120             130             140             150             160             170
         CCT GGA GGG AGC CTG CGT CTC TCT TGT GCA GCA AGC GGC TTC ACC TTT TCC TCT TAC
         GGA CCT CCC TCG GAC GCA GAG AGA ACA CGT CGT TCG CCG AAG TGG AAA AGG AGA ATG
         P   G   G   S   L   R   L   S   C   A   A   S   G   F   T   F   S   S   Y>

180             190             200             210             220             230
         GGT ATG TCC TGG GTG CGG CAG GCA CCT GGG AAG GGC CTG GAG TGG GTG GCA ACC ATT
         CCA TAC AGG ACC CAC GCC GTC CGT GGA CCC TTC CCG GAC CTC ACC CAC CGT TGG TAA
         G   M   S   W   V   R   Q   A   P   G   K   G   L   E   W   V   A   T   I>

BspEI        250             260             270             280
         ACG TCC GGA GGC AGC TAT ACA TAC TAC CCG GAC ACC GTC AAG GGC CGT TTC ACC ATT
         TGC AGG CCT CCG TCG ATA TGT ATG ATG GGC CTG TGG CAG TTC CCG GCA AAG TGG TAA
         T   S   G   G   S   Y   T   Y   Y   P   D   T   V   K   G   R   F   T   I>

290   XmaI   300             310             320             330             340
         TCC CGG GAC AAT GCA AAG AAT AGC CTT TAC CTC CAG ATG AAC TCT CTC CGC GCA GAG
         AGG GCC CTG TTA CGT TTC TTA TCG GAA ATG GAG GTC TAC TTG AGA GAG GCG CGT CTC
         S   R   D   N   A   K   N   S   L   Y   L   Q   M   N   S   L   R   A   E>

350             360             370             380    MluI  390             400
         GAC ACA GCA GTC TAT TAC TGT GCA CGG ATC GGC GAA GAC GCG TTG GAC TAC TGG GGA
         CTG TGT CGT CAG ATA ATG ACA CGT GCC TAG CCG CTT CTG CGC AAC CTG ATG ACC CCT
         D   T   A   V   Y   Y   C   A   R   I   G   E   D   A   L   D   Y   W   G>

410             420             430             440   ApaI   450
         CAG GGG ACC CTT GTG ACA GTC TCC TCT GCT TCT ACA AAG GGC CCA AGA AA
         GTC CCC TGG GAA CAC TGT CAG AGG AGA CGA AGA TGT TTC CCG GGT TCT TT
         Q   G   T   L   V   T   V   S   S   A   S   T   K   G   P>
``` gL1 sequence  (SEQ ID NO:24)

```
          SfuI          20              30              40              50              60
        GGATGATTCG AAGCCGCCAC C ATG AGG ACC CCT GCT CAG ATT CTT GGC TTC TTG TTG CTC
        CCTACTAAGC TTCGGCGGTG G TAC TCC TGG GGA CGA GTC TAA GAA CCG AAG AAC AAC GAG
                                 M   R   T   P   A   Q   I   L   G   F   L   L   L>

70              80    EcoRV   90             100             110
        TTG TTT CCA GGT ACC AGA TGT GAT ATC CAG ATG ACC CAG AGT CCA AGC AGT CTC TCC
        AAC AAA GGT CCA TGG TCT ACA CTA TAG GTC TAC TGG GTC TCA GGT TCG TCA GAG AGG
        L   F   P   G   T   R   C   D   I   Q   M   T   Q   S   P   S   S   L   S>

120             130             140             150             160             170
        GCC AGC GTA GGC GAT CGT GTG ACT ATT ACC TGT CGT GCC AGT CAG GAC ATC GCG GGT
        CGG TCG CAT CCG CTA GCA CAC TGA TAA TGG ACA GCA CGG TCA GTC CTG TAG CGC CCA
        A   S   V   G   D   R   V   T   I   T   C   R   A   S   Q   D   I   A   G>

180             190             200             210             220             230
        AGC CTG AAC TGG TAT CAG CAA AAA CCG GGC AAA GCC CCC AAG CGC CTC ATC TAT GCG
        TCG GAC TTG ACC ATA GTC GTT TTT GGC CCG TTT CGG GGG TTC GCG GAG TAG ATA CGC
        S   L   N   W   Y   Q   Q   K   P   G   K   A   P   K   R   L   I   Y   A>

AatII   240             250             260             270             280
        ACG TCC AGC CTG GAT AGC GGT GTG CCA TCT CGT TTC AGT GGC AGT GGC AGC GGT ACT
        TGC AGG TCG GAC CTA TCG CCA CAC GGT AGA GCA AAG TCA CCG TCA CCG TCG CCA TGA
        T   S   S   L   D   S   G   V   P   S   R   F   S   G   S   G   S   G   T>

290             300             BsmBI   320             330             340
        GAA TTT ACC CTC ACA ATT TCG TCT CTC CAG CCG GAA GAT TTC GCC ACT TAC TAT TGT
        CTT AAA TGG GAG TGT TAA AGC AGA GAG GTC GGC CTT CTA AAG CGG TGA ATG ATA ACA
        E   F   T   L   T   I   S   S   L   Q   P   E   D   F   A   T   Y   Y   C>

```
CTG CAA TAT GGC AGC TTC CCT CCG ACC TTC GGT CAG GGC ACT AAA GTA GAA ATC AAA
GAC GTT ATA CCG TCG AAG GGA GGC TGG AAG CCA GTC CCG TGA TTT CAT CTT TAG TTT
 L   Q   Y   G   S   F   P   P   T   F   G   Q   G   T   K   V   E   I   K>

BsiWI 410
CGT ACG GC GTGC
GCA TGC CG CACG
 R   T>
```

FIG. 10 cont.

Figure 11: Oligonucleotides for gene assembly gL1 F1 (SEQ ID NO:25)
GGATGATTCGAAGCCGCCAC gL1 F2 (SEQ ID NO:26)
TCCAGGTACCAGATGTGATATCCAGATGACCCAGAGTCCAAGCAGTCTCTCCGCCAGCGTAGGCGATCGTG
TGACTATTACCTGTC gL1 F3 (SEQ ID NO:27)
CAAAAACCGGGCAAAGCCCCCAAGCGCCTCATCTATGCGACGTCCAGCCTGGATAGCGGTGTGCCATCTCG
TTTCAGTGGCAGTGGC gL1 F4 (SEQ ID NO:28)
AGATTTCGCCACTTACTATTGTCTGCAATATGGCAGCTTCCCTCCGACCTTCGGTCAGGGCACTAAAGTAGA
AATCAAACGTACGGCGTGC gL1 R1 (SEQ ID NO:29)
GCACGCCGTACGTTTGATTTC gL1 R2 (SEQ ID NO:30)
GACAATAGTAAGTGGCGAAATCTTCCGGCTGGAGAGACGAAATTGTGAGGGTAAATTCAGTACCGCTGCCA
CTGCCACTGAAACGAG gL1 R3 (SEQ ID NO:31)
GGGGCTTTGCCCGGTTTTTGCTGATACCAGTTCAGGCTACCCGCGATGTCCTGACTGGCACGACAGGTAAT
AGTCACACGATC gL1 R4 (SEQ ID NO:32)
GATATCACATCTGGTACCTGGAAACAAGAGCAACAAGAAGCCAAGAATCTGAGCAGGGGTCCTCATGGTGG
CGGCTTCGAATCATCC gH1 F1 (SEQ ID NO:33)
GAATAAAAGCTTGCCGCCACC gH1 F2 (SEQ ID NO:34)
TCCAGTGTGAGGTGCAGCTGGTCGAGTCTGGAGGCGGGCTTGTCCAGCCTGGAGGGAGCCTGCGTCTCTC
TTGTGCAGCAAGCGGCTTCAC gH1 F3 (SEQ ID NO:35)
AGTGGGTGGCAACCATTACGTCCGGAGGCAGCTATACATACTACCCGGACACCGTCAAGGGCCGTTTCACC
ATTTCCCGGGACAATGCAA gH1 F4 (SEQ ID NO:36)
CTATTACTGTGCACGGATCGGCGAAGACGCGTTGGACTACTGGGGACAGGGGACCCTTGTGACAGTCTCCT
CTGCTTCTACAAAGGGCCCAAGAAA gH1 R1 (SEQ ID NO:37)
TTTCTTGGGCCCTTTGTAGAAG gH1 R2 (SEQ ID NO:38)
CCGATCCGTGCACAGTAATAGACTGCTGTGTCCTCTGCGCGGAGAGAGTTCATCTGGAGGTAAAGGCTATT
CTTTGCATTGTCCCGGGAAATGG gH1 R3 (SEQ ID NO:39)
ACGTAATGGTTGCCACCCACTCCAGGCCCTTCCCAGGTGCCTGCCGCACCCAGGACATACCGTAAGAGGAA
AAGGTGAAGCCGCTTGCTGCACA gH1 R4 (SEQ ID NO:40)
CAGCTGCACCTCACACTGGACACCTTTTAAAATGAGGGCAAGGAAAACCCAGTTTAACCACATCTTCATGGT
GGCGGCAAGCTTTTATTC

Plasmid pCR2.1(gH1) and pCR2.1(gL1)
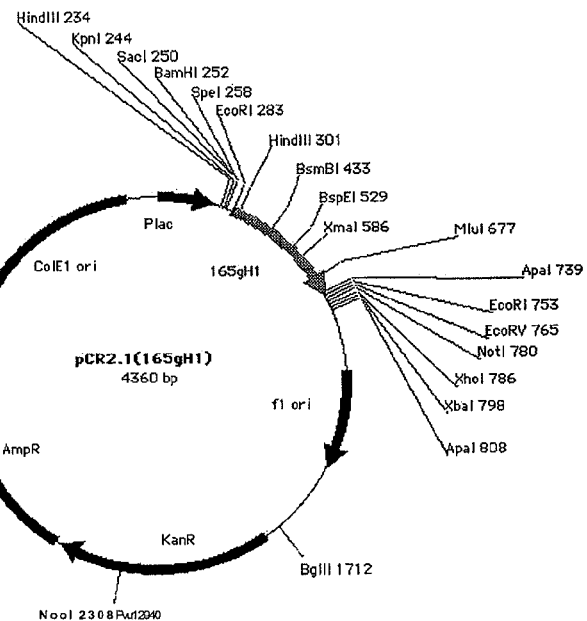
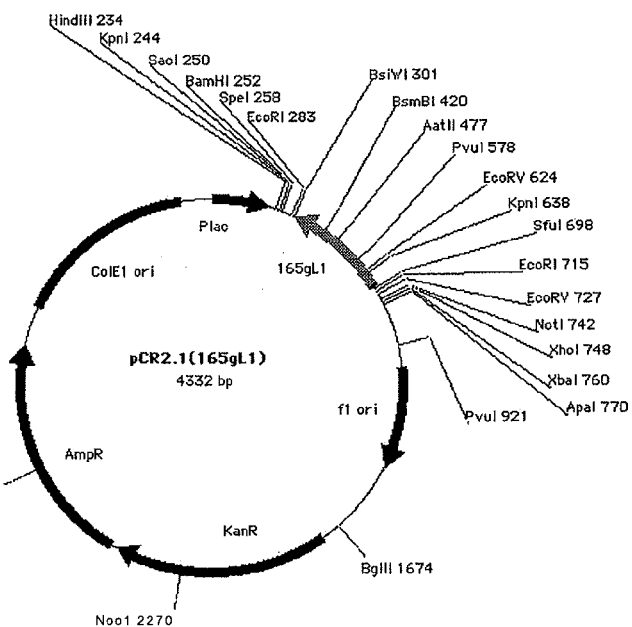
FIG. 12A & B

Figure 13: Oligonucleotide cassettes for construction of gH2, gH3, gL2, gH3 gH2 cassette     (SEQ ID NO: 41)

```
    XmaI      10            20            30            40            50
    TCC CGG GAC AAT GCA AAG AAT ACC CTT TAC CTC CAG ATG AAC TCT CTC CGC GCA GAG
    AGG GCC CTG TTA CGT TTC TTA TGG GAA ATG GAG GTC TAC TTG AGA GAG GCG CGT CTC
        S   R   D   N   A   K   N   T   L   Y   L   Q   M   N   S   L   R   A   E>

60            70            80            90          MluI
    GAC ACA GCA GTC TAT TAC TGT GTA CGG ATC GGC GAA GAC GCG TTG
    CTG TGT CGT CAG ATA ATG ACA CAT GCC TAG CCG CTT CTG CGC AAC
     D   T   A   V   Y   Y   C   V   R   I   G   E   D   A   L>
``` gH3 cassette     (SEQ ID NO:42)

```
    BspEI     10            20            30            40            50
    TCC GGA GGC AGC TAT ACA TAC TAC GTG GAC AGC GTC AAG GGC CGT TTC ACC ATT TCC
    AGG CCT CCG TCG ATA TGT ATG ATG CAC CTG TCG CAG TTC CCG GCA AAG TGG TAA AGG
        S   G   G   S   Y   T   Y   Y   V   D   S   V   K   G   R   F   T   I   S>

XmaI
    CGG GAC
    GCC CTG
     R   D>
``` gL2 cassette (SEQ ID NO:43)

```
    AatII     10            20            30            40            50
    GCG ACG TCC AGC CTG GAT AGC GGT GTG CCA AAA CGT TTC AGT GGC AGT CGC AGC GGT
    CGC TGC AGG TCG GAC CTA TCG CCA CAC GGT TTT GCA AAG TCA CCG TCA GCG TCG CCA
      A   T   S   S   L   D   S   G   V   P   K   R   F   S   G   S   R   S   G>

60            70            80    BsmBI   90
    TCT GAC TAT ACC CTC ACA ATT TCG TCT CTC CAG
    AGA CTG ATA TGG GAG TGT TAA AGC AGA GAG GTC
     S   D   Y   T   L   T   I   S   S   L   Q>
``` gL3 cassette (SEQ ID NO:44)

```
    PvuI      10            20            30            40            50
    GGC GAT CGT GTG ACT ATT ACC TGT CGT GCC AGT CAG GAC ATC GCG GGT AGC CTG AAC
    CCG CTA GCA CAC TGA TAA TGG ACA GCA CGG TCA GTC CTG TAG CGC CCA TCG GAC TTG
        G   D   R   V   T   I   T   C   R   A   S   Q   D   I   A   G   S   L   N>

60            70            80            90           100           AatII
    TGG TTG CAG CAA AAA CCG GGC AAA GCC ATC AAG CGC CTC ATC TAT GCG ACG TCC
    ACC AAC GTC GTT TTT GGC CCG TTT CGG TAG TTC GCG GAG TAG ATA CGC TGC AGG
     W   L   Q   Q   K   P   G   K   A   I   K   R   L   I   Y   A   T   S>
```

Underlined residues represent changed amino acids compared to the parent sequence.

Figure 14: Oligonucleotides pairs for gH2, gH3, gL2, gL3 construction gH2T    (SEQ ID NO:45)
CCGGGACAATGCAAAGAATACCCTTTACCTCCAGATGAACTCTCTCCGCGCAGAGGACACAGCAGT
CTATTACTGTGTACGGATCGGCGAAGA gH2B    (SEQ ID NO:46)
CGCGTCTTCGCCGATCCGTACACAGTAATAGACTGCTGTGTCCTCTGCGCGGAGAGAGTTCATCTG
GAGGTAAAGGGTATTCTTTGCATTGTC gH3T    (SEQ ID NO:47)
CCGGAGGCAGCTATACATACTACGTGGACAGCGTCAAGGGCCGTTTCACCATTTC gH3B    (SEQ ID NO:48)
CCGGGAAATGGTGAAACGGCCCTTGACGCTGTCCACGTAGTATGTATAGCTGCCT gL2T    (SEQ ID NO:49)
CCAGCCTGGATAGCGGTGTGCCAAAACGTTTCAGTGGCAGTCGCAGCGGTTCTGACTATACCCTC
ACAATTTCGTCTCT gL2B    (SEQ ID NO:50)
CTGGAGAGACGAAATTGTGAGGGTATAGTCAGAACCGCTGCGACTGCCACTGAAACGTTTTGGCA
CACCGCTATCCAGGCTGGACGT gL3T    (SEQ ID NO:51)
CGTGTGACTATTACCTGTCGTGCCAGTCAGGACATCGCGGGTAGCCTGAACTGGTTGCAGCAAAA
ACCGGGCAAAGCCATCAAGCGCCTCATCTATGCGACGT gH3B    (SEQ ID NO:52)
CGCATAGATGAGGCGCTTGATGGCTTTGCCCGGTTTTTGCTGCAACCAGTTCAGGCTACCCGCGAT
GTCCTGACTGGCACGACAGGTAATAGTCACACGAT

*CHO expression plasmids*
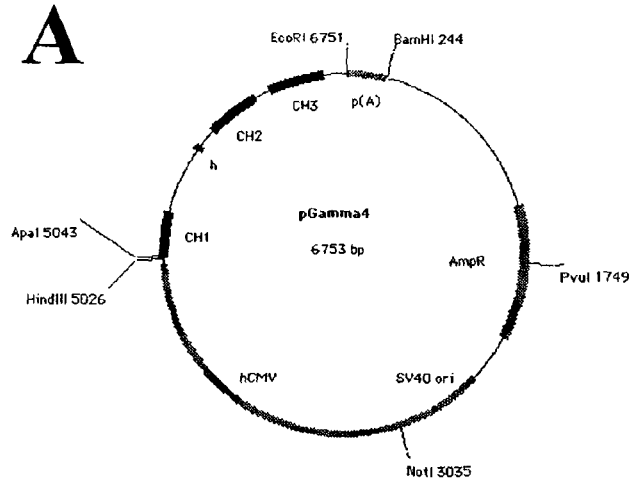
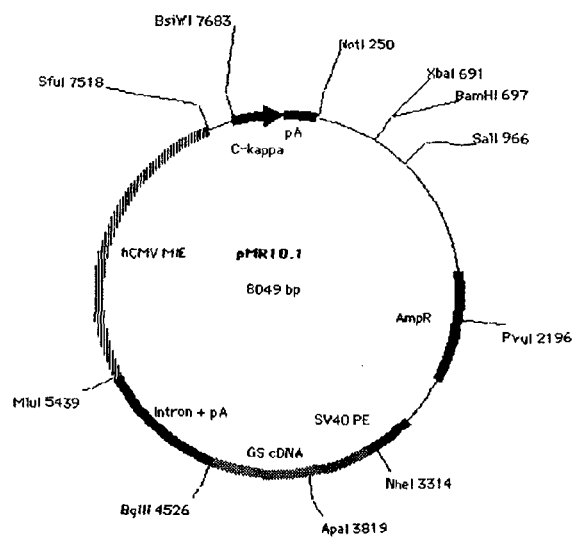
FIG. 15A &B pTTOD(Fab' IGS-3) map

Figure 17: IGS Sequences (SEQ ID NO:53)

IGS-1;   Intergenic space = -1

G,AGC,TCA,CCA,GTA,ACA,AAA,AGT,TTT,AAT,AGA,GGA,GAG,TGT,TAATG,AAG,AAG,ACT,GCT,ATA,GCA,ATT,G

S   S   P   V   T   K   S   F   N   R   G   E   C   *M   K   K   T   A   I   A   I
End of c-Kappa sequence ->                                    Start of OmpA sequence ->

(SEQ ID NO:54)

IGS-2;   Intergenic space = +1

G,AGC,TCA,CCA,GTA,ACA,AAA,AGT,TTT,AAT,AGA,GGG,GAG,TGT,TAA,AATG,AAG,AAG,ACT,GCT,ATA,GCA,ATT,G

S   S   P   V   T   K   S   F   N   R   G   E   C   *   M   K   K   T   A   I   A   I (SEQ ID NO:55)

IGS-3;   Intergenic space = +13

G,AGC,TCA,CCA,GTA,ACA,AAA,AGC,TTT,AAT,AGA,GGA,GAG,TGT,TGA GGAGGAAAAAAAATG,AAG,AAA,ACT,GCT,ATA,GCA,ATT,G

S   S   P   V   T   K   S   F   N   R   G   E   C   *                       M   K   K   T   A   I   A   I

Figure 18: Fermentation of Fab'
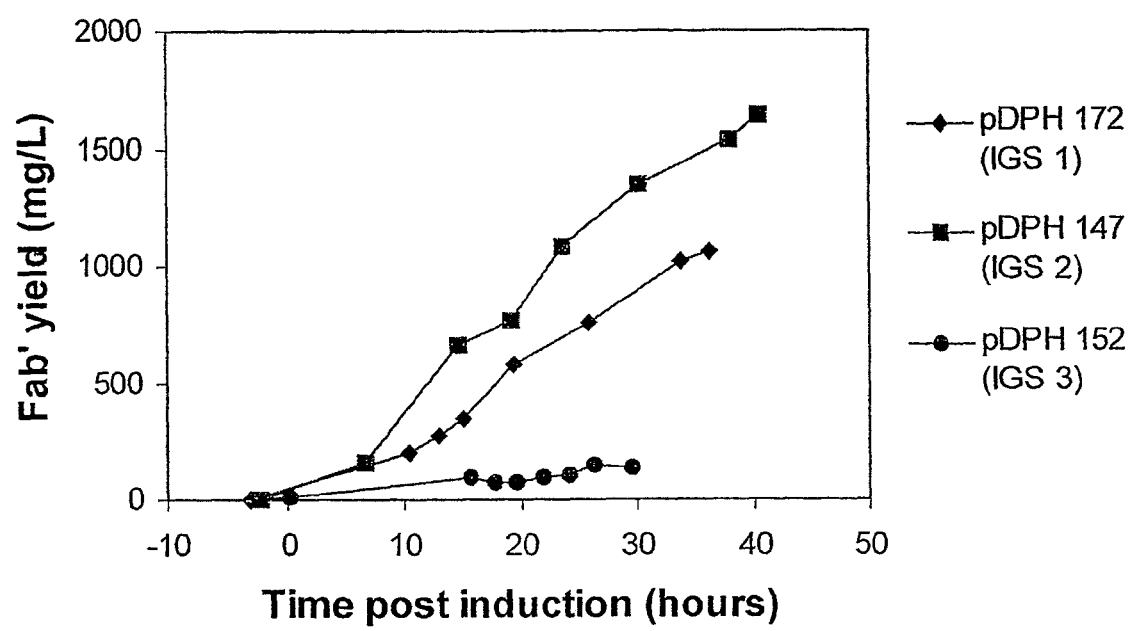

Figure 19: Coding and flanking sequence of CDP791 Fab'    (SEQ ID NO:56)

```
              10         20         30         40         50         60         70
         AATTCTCATG TTTGACAGCT TATCATCGAC TGCACGGTGC ACCAATGCTT CTGGCGTCAG GCAGCCATCG
         TTAAGAGTAC AAACTGTCGA ATAGTAGCTG ACGTGCCACG TGGTTACGAA GACCGCAGTC CGTCGGTAGC 80         90        100        110        120        130        140
         GAAGCTGTGG TATGGCTGTG CAGGTCGTAA ATCACTGCAT AATTCCTGTC GCTCAAGGCG CACTCCCGTT
         CTTCGACACC ATACCGACAC GTCCAGCATT TAGTGACGTA TTAAGGACAG CGAGTTCCGC GTGAGGGCAA 150        160        170        180        190        200        210
         CTGGATAATG TTTTTTGCGC CGACATCATA ACGGTTCTGG CAAATATTCT GAAATGAGCT GTTGACAATT
         GACCTATTAC AAAAAACGCG GCTGTAGTAT TGCCAAGACC GTTTATAAGA CTTTACTCGA CAACTGTTAA 220        230        240        250        260        270        280
         AATCATCGGC TCGTATAATG TGTGGAATTG TGAGCGGATA ACAATTTCAC ACAGGAAACA GCGATGAGCT
         TTAGTAGCCG AGCATATTAC ACACCTTAAC ACTCGCCTAT TGTTAAAGTG TGTCCTTTGT CGCTACTCGA 290        300        310        320        330        340
         TGGCTGCAGG TCGAGTTCTA GATAACGAGG CGTAAAAA ATG AAA AAG ACA GCT ATC GCA ATT GCA
         ACCGACGTCC AGCTCAAGAT CTATTGCTCC GCATTTTT TAC TTT TTC TGT CGA TAG CGT TAA CGT
                                                   M   K   K   T   A   I   A   I   A>

350            360            370            380            390            400
         GTG GCC TTG GCT GGT TTC GCT ACC GTA GCG CAA GCT GAT ATC CAG ATG ACC CAG AGT
         CAC CGG AAC CGA CCA AAG CGA TGG CAT CGC GTT CGA CTA TAG GTC TAC TGG GTC TCA
          V   A   L   A   G   F   A   T   V   A   Q   A   D   I   Q   M   T   Q   S>

410            420            430            440            450
         CCA AGC AGT CTC TCC GCC AGC GTA GGC GAT CGT GTG ACT ATT ACC TGT CGT GCC AGT
         GGT TCG TCA GAG AGG CGG TCG CAT CCG CTA GCA CAC TGA TAA TGG ACA GCA CGG TCA
          P   S   S   L   S   A   S   V   G   D   R   V   T   I   T   C   R   A   S>

460        470            480            490            500            510
         CAG GAC ATC GCG GGT AGC CTG AAC TGG TTG CAG CAA AAA CCG GGC AAA GCC ATC AAG
         GTC CTG TAG CGC CCA TCG GAC TTG ACC AAC GTC GTT TTT GGC CCG TTT CGG TAG TTC
          Q   D   I   A   G   S   L   N   W   L   Q   Q   K   P   G   K   A   I   K>

520            530            540            550            560            570
         CGC CTC ATC TAT GCG ACG TCC AGC CTG GAT AGC GGT GTG CCA AAA CGT TTC AGT GGC
         GCG GAG TAG ATA CGC TGC AGG TCG GAC CTA TCG CCA CAC GGT TTT GCA AAG TCA CCG
          R   L   I   Y   A   T   S   S   L   D   S   G   V   P   K   R   F   S   G>

580            590            600            610            620            630
         AGT CGC AGC GGT TCT GAC TAT ACC CTC ACA ATT TCG TCT CTC CAG CCG GAA GAT TTC
         TCA GCG TCG CCA AGA CTG ATA TGG GAG TGT TAA AGC AGA GAG GTC GGC CTT CTA AAG
          S   R   S   G   S   D   Y   T   L   T   I   S   S   L   Q   P   E   D   F>

640            650            660            670            680
         GCC ACT TAC TAT TGT CTG CAA TAT GGC AGC TTC CCT CCG ACC TTC GGT CAG GGC ACT
         CGG TGA ATG ATA ACA GAC GTT ATA CCG TCG AAG GGA GGC TGG AAG CCA GTC CCG TGA
          A   T   Y   Y   C   L   Q   Y   G   S   F   P   P   T   F   G   Q   G   T>

690            700            710            720            730            740
         AAA GTA GAA ATC AAA CGT ACG GTA GCG GCC CCA TCT GTC TTC ATC TTC CCG CCA TCT
         TTT CAT CTT TAG TTT GCA TGC CAT CGC CGG GGT AGA CAG AAG TAG AAG GGC GGT AGA
          K   V   E   I   K   R   T   V   A   A   P   S   V   F   I   F   P   P   S>

750            760            770            780            790            800
         GAT GAG CAG TTG AAA TCT GGA ACT GCC TCT GTT GTG TGC CTG CTG AAT AAC TTC TAT
         CTA CTC GTC AAC TTT AGA CCT TGA CGG AGA CAA CAC ACG GAC GAC TTA TTG AAG ATA
          D   E   Q   L   K   S   G   T   A   S   V   V   C   L   L   N   N   F   Y>

810            820            830            840            850
         CCC AGA GAG GCC AAA GTA CAG TGG AAG GTG GAT AAC GCC CTC CAA TCG GGT AAC TCC
         GGG TCT CTC CGG TTT CAT GTC ACC TTC CAC CTA TTG CGG GAG GTT AGC CCA TTG AGG
          P   R   E   A   K   V   Q   W   K   V   D   N   A   L   Q   S   G   N   S>

860            870            880            890            900            910
         CAG GAG AGT GTC ACA GAG CAG GAC AGC AAG GAC AGC ACC TAC AGC CTC AGC AGC ACC
         GTC CTC TCA CAG TGT CTC GTC CTG TCG TTC CTG TCG TGG ATG TCG GAG TCG TCG TGG
          Q   E   S   V   T   E   Q   D   S   K   D   S   T   Y   S   L   S   S   T>
```

FIG. 19

```
           920         930         940         950         960         970
      CTG ACG CTG AGC AAA GCA GAC TAC GAG AAA CAC AAA GTC TAC GCC TGC GAA GTC ACC
      GAC TGC GAC TCG TTT CGT CTG ATG CTC TTT GTG TTT CAG ATG CGG ACG CTT CAG TGG
       L   T   L   S   K   A   D   Y   E   K   H   K   V   Y   A   C   E   V   T>

980         990        1000        1010        1020        1030
      CAT CAG GGC CTG AGC TCA CCA GTA ACA AAA AGT TTT AAT AGA GGG GAG TGT TAA A ATG
      GTA GTC CCG GAC TCG AGT GGT CAT TGT TTT TCA AAA TTA TCT CCC CTC ACA ATT T TAC
       H   Q   G   L   S   S   P   V   T   K   S   F   N   R   G   E   C   *>
                                                                                M>

1040        1050        1060        1070        1080
      AAG AAG ACT GCT ATA GCA ATT GCA GTG GCG CTA GCT GGT TTC GCC ACC GTG GCG CAA
      TTC TTC TGA CGA TAT CGT TAA CGT CAC CGC GAT CGA CCA AAG CGG TGG CAC CGC GTT
       K   K   T   A   I   A   I   A   V   A   L   A   G   F   A   T   V   A   Q>

1090        1100        1110        1120        1130        1140
      GCT GAG GTT CAG CTG GTC GAG TCT GGA GGC GGG CTT GTC CAG CCT GGA GGG AGC CTG
      CGA CTC CAA GTC GAC CAG CTC AGA CCT CCG CCC GAA CAG GTC GGA CCT CCC TCG GAC
       A   E   V   Q   L   V   E   S   G   G   G   L   V   Q   P   G   G   S   L>

1150        1160        1170        1180        1190        1200
      CGT CTC TCT TGT GCA GCA AGC GGC TTC ACC TTT TCC TCT TAC GGT ATG TCC TGG GTG
      GCA GAG AGA ACA CGT CGT TCG CCG AAG TGG AAA AGG AGA ATG CCA TAC AGG ACC CAC
       R   L   S   C   A   A   S   G   F   T   F   S   S   Y   G   M   S   W   V>

1210        1220        1230        1240        1250
      CGG CAG GCA CCT GGG AAG GGC CTG GAG TGG GTG GCA ACC ATT ACG TCC GGA GGC AGC
      GCC GTC CGT GGA CCC TTC CCG GAC CTC ACC CAC CGT TGG TAA TGC AGG CCT CCG TCG
       R   Q   A   P   G   K   G   L   E   W   V   A   T   I   T   S   G   G   S>

1260        1270        1280        1290        1300        1310
      TAT ACA TAC TAC GTG GAC AGC GTC AAG GGC CGT TTC ACC ATT TCC CGG GAC AAT GCA
      ATA TGT ATG ATG CAC CTG TCG CAG TTC CCG GCA AAG TGG TAA AGG GCC CTG TTA CGT
       Y   T   Y   Y   V   D   S   V   K   G   R   F   T   I   S   R   D   N   A>

1320        1330        1340        1350        1360        1370
      AAG AAT ACC CTT TAC CTC CAG ATG AAC TCT CTC CGC GCA GAG GAC ACA GCA GTC TAT
      TTC TTA TGG GAA ATG GAG GTC TAC TTG AGA GAG GCG CGT CTC CTG TGT CGT CAG ATA
       K   N   T   L   Y   L   Q   M   N   S   L   R   A   E   D   T   A   V   Y>

1380        1390        1400        1410        1420
      TAC TGT GTA CGG ATC GGC GAA GAC GCG TTG GAC TAC TGG GGA CAG GGG ACC CTT GTG
      ATG ACA CAT GCC TAG CCG CTT CTG CGC AAC CTG ATG ACC CCT GTC CCC TGG GAA CAC
       Y   C   V   R   I   G   E   D   A   L   D   Y   W   G   Q   G   T   L   V>

1430        1440        1450        1460        1470        1480
      ACA GTC TCC TCT GCT TCT ACA AAG GGC CCA TCG GTC TTC CCC CTG GCA CCC TCC TCC
      TGT CAG AGG AGA CGA AGA TGT TTC CCG GGT AGC CAG AAG GGG GAC CGT GGG AGG AGG
       T   V   S   S   A   S   T   K   G   P   S   V   F   P   L   A   P   S   S>

1490        1500        1510        1520        1530        1540
      AAG AGC ACC TCT GGG GGC ACA GCG GCC CTG GGC TGC CTG GTC AAG GAC TAC TTC CCC
      TTC TCG TGG AGA CCC CCG TGT CGC CGG GAC CCG ACG GAC CAG TTC CTG ATG AAG GGG
       K   S   T   S   G   G   T   A   A   L   G   C   L   V   K   D   Y   F   P>

1550        1560        1570        1580        1590        1600
      GAA CCG GTG ACG GTG TCG TGG AAC TCA GGC GCC CTG ACC AGC GGC GTG CAC ACC TTC
      CTT GGC CAC TGC CAC AGC ACC TTG AGT CCG CGG GAC TGG TCG CCG CAC GTG TGG AAG
       E   P   V   T   V   S   W   N   S   G   A   L   T   S   G   V   H   T   F>

1610        1620        1630        1640        1650
      CCG GCT GTC CTA CAG TCC TCA GGA CTC TAC TCC CTC AGC AGC GTG GTG ACC GTG CCC
      GGC CGA CAG GAT GTC AGG AGT CCT GAG ATG AGG GAG TCG TCG CAC CAC TGG CAC GGG
       P   A   V   L   Q   S   S   G   L   Y   S   L   S   S   V   V   T   V   P>

1660        1670        1680        1690        1700        1710
      TCC AGC AGC TTG GGC ACC CAG ACC TAC ATC TGC AAC GTG AAT CAC AAG CCC AGC AAC
      AGG TCG TCG AAC CCG TGG GTC TGG ATG TAG ACG TTG CAC TTA GTG TTC GGG TCG TTG
       S   S   S   L   G   T   Q   T   Y   I   C   N   V   N   H   K   P   S   N>

1720        1730        1740        1750        1760        1770
      ACC AAG GTC GAC AAG AAA GTT GAG CCC AAA TCT TGT GAC AAA ACT CAC ACA TGC GCC
      TGG TTC CAG CTG TTC TTT CAA CTC GGG TTT AGA ACA CTG TTT TGA GTG TGT ACG CGG
```

FIG. 19 cont.

```
          T   K   V   D   K   K   V   E   P   K   S   C   D   K   T   H   T   C   A>
          1780       1790       1800       1810       1820       1830       1840
     GCG TGA TGA GGATCCAAGC TTGCGGCCGC GAATTCACTG GCCGTCGTTT TACAACGTCG TGACTGGGAA
     CGC ACT ACT CCTAGGTTCG AACGCCGGCG CTTAAGTGAC CGGCAGCAAA ATGTTGCAGC ACTGACCCTT
      A   *>
          1850       1860       1870       1880       1890       1900       1910
     AACCCTGGCG TTACCCAACT TAATCGCCTT GCAGCACATC CCCCTTTCGC CAGCTCGCGT AATAGCGAAG
     TTGGGACCGC AATGGGTTGA ATTAGCGGAA CGTCGTGTAG GGGGAAAGCG GTCGAGCGCA TTATCGCTTC 1920       1930       1940       1950       1960       1970       1980
     AGGCCCGCAC CGATCGCCCT TCCCAACAGT TGCGCAGCCT GAATGGCGAA TGGCGCCTGA TGCGGTATTT
     TCCGGGCGTG GCTAGCGGGA AGGGTTGTCA ACGCGTCGGA CTTACCGCTT ACCGCGGACT ACGCCATAAA 1990       2000
     TCTCCTTACG CATCTGTGCG
     AGAGGAATGC GTAGACACGC
```

FIG. 19 cont.

Figure 20: Radioimmunoassay Results
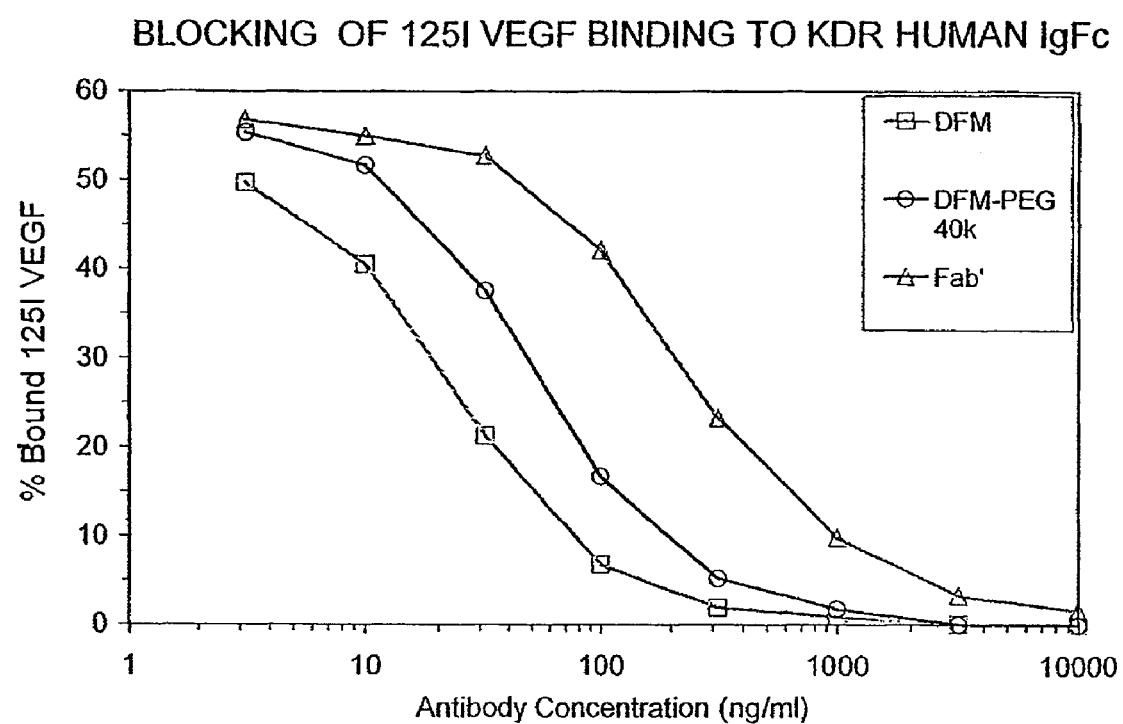

Figure 21: Protein sequence of gH3-grafted heavy chain

Heavy Chain antibody sequence (SEQ ID NO:57)
EVQLVESGGGLVQPGGSLRLSCAASGFTFSSYGMSWVRQAPGKGLEWVATITSGGSY
TYYVDSVKGRFTISRDNAKNTLYLQMNSLRAEDTAVYYCVRIGEDALDYWGQGTLVT
VSSASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPSCPA
PEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLGK*

BIOLOGICAL PRODUCTS

CROSS-REFERENCE TO RELATED APPLICATIONS

The present application is a divisional of U.S. application Ser. No. 10/492,228, filed Feb. 15, 2005 now U.S. Pat. No. 7,452,976 which is a 35 U.S.C. 371 National Stage Application of International Application No. PCT/GB02/04619, International Filing Date: Oct. 10, 2002, which claims priority under 35 U.S.C. §119(a) to Great Britain Application No. 0124317.9, Filing Date: Oct. 10, 2001, all of which are incorporated herein by reference in their entirety.

The present invention relates to an antibody molecule having specificity for antigenic determinants of human kinase insert domain-containing receptor (KDR). The antibody molecule binds KDR with greater affinity than human vascular endothelial growth factor (VEGF) and prevents the interaction between VEGF and KDR. The present invention also relates to the therapeutic uses of the antibody molecule and methods for producing the antibody molecule.

This invention relates to antibody molecules. In an antibody molecule, there are two heavy chains and two light chains. Each heavy chain and each light chain has at its N-terminal end a variable domain. Each variable domain is composed of four framework regions (FRs) alternating with three complementarity determining regions (CDRs). The CDRs determine the antigen binding specificity of antibodies and are relatively short peptide sequences carried on the framework regions of the variable domains. The residues in the variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering, corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDRH1), residues 50-65 (CDRH2) and residues 95-102 (CDRH3) according to the Kabat numbering.

The CDRs of the light chain variable domain are located at residues 24-34 (CDRL1), residues 50-56 (CDRL2) and residues 89-97 (CDRL3) according to the Kabat numbering.

Construction of CDR-grafted antibodies is described in European Patent Application EP-A-0239400, which discloses a process in which the CDRs of a mouse monoclonal antibody (Mab) are grafted onto the framework regions of the variable domains of a human immunoglobulin by site directed mutagenesis using long oligonucleotides.

The earliest work on humanising Mabs by CDR-grafting was carried out on Mabs recognising synthetic antigens, such as NP. However, examples in which a mouse Mab recognising lysozyme and a rat Mab recognising an antigen on human T-cells were humanised by CDR-grafting have been described by Verhoeyen et al. (Science, 239, 1534-1536, 1988) and Riechmann et al. (Nature, 332, 323-324, 1988), respectively.

Riechmann et al. found that the transfer of the CDRs alone (as defined by Kabat (Kabat et al. (supra) and Wu et al., J. Exp. Med., 132, 211-250, 1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application No. WO 90/07861.

A number of reviews discussing CDR-grafted antibodies have been published, including Vaughan et al. (Nature Biotechnology, 16, 535-539, 1998).

VEGF is a homodimeric glycoprotein of two 23 kD subunits with structural similarity to PDGF. It has an important developmental role in vasculogenesis, the establishment of a system of new blood vessels, and is involved in angiogenesis, the formation of new vessels from pre-existing ones. Angiogenesis involves the proliferation, migration and tissue infiltration of capillary endothelial cells from pre-existing blood vessels. As well as playing an important role in normal physiological processes, such as embryonic development, follicular growth (including corpus luteum formation) and wound healing, angiogenesis occurs in a number of pathological conditions including inflammation, psoriasis, rheumatoid arthritis and tumour growth and metastasis (Folkman, J and Klagsbrun, M., Science, 235:442-447, 1987). For example, it is widely believed that tumours are incapable of growing beyond a certain size unless they are provided with a dedicated blood supply via angiogenesis.

VEGF is distinct from other factors implicated as possible regulators of angiogenesis in vivo in that it is an endothelial cell-specific angiogenesis inducer.

Five different monomeric isoforms of VEGF exist, resulting from alternative splicing of mRNA. The isoforms include two membrane bound forms ($VEGF_{206}$ and $VEGF_{189}$) and three soluble forms ($VEGF_{165}$, $VEGF_{121}$ and $VEGF_{145}$). In all tissues except human placenta, $VEGF_{165}$ is the most abundant isoform.

The effects of VEGF are mediated through its interaction with two high affinity tyrosine kinase receptors, fms-like tyrosine kinase receptor (FLT-1 or VEGFR-1, Shibuya M. et al., Oncogene, 5, 519-524, 1990) and KDR (or VEGFR-2, Terman et al., Oncogene, 6, 1677-1683, 1991). Both KDR and FLT-1 are membrane-spanning receptors that each contain seven immunoglobulin-like domains in the extracellular ligand-binding region, an intracellular tyrosine kinase domain and a transmembrane domain. The transmembrane domain serves to anchor the receptor in the cell membrane of the cells in which it is expressed.

There are several reports of the over-expression of both VEGF and its receptors within tumours, both at the RNA and protein levels (Dvorak et al., Curr. Top. Microbiol. Immunol., 237, 97, 1999). VEGF expression is upregulated in response to hypoxia, which frequently occurs within tumours, and increased concentration of ligand induces the expression of its receptors. Examples of studies showing increased KDR expression in human tumours include: breast cancer (Brown et al., Hum. Pathol., 26, 86, 1995); colon cancer (Takahashi et al., Cancer Res., 55, 3964, 1995); renal cancer (Takahashi et al, BBRC 257, 855, 1999) and adenocarcinoma of the gastrointestinal tract (Brown et al., Cancer Res., 53, 4727, 1993). In a more recent study using an antibody specifically recognising VEGF bound to KDR, upregulation of the VEGF/KDR angiogenic pathway in non-small cell lung cancer was observed (Koukourakis et al., Cancer Res., 60, 3088, 2000).

A number of pieces of experimental evidence demonstrate the causal link between VEGF activity and tumour angiogenesis in vivo. Kim et al. injected an anti-VEGF neutralising Mab into tumour-bearing nude mice and showed suppressed tumour growth (Nature 362, 841, 1993). Retroviral expression of a dominant negative mouse KDR (FLK-1) also inhibited tumour growth in mice (Millauer et al., Nature, 367, 576, 1993). Similarly, VEGF antisense (Cheng et al., PNAS, 93, 8502, 1996), anti-FLK-1 antibodies (Witte et al., Cancer Metast. Rev., 17, 155, 1998) and expression of soluble FLT-1 (Goldman et al., PNAS, 95, 8795, 1998) all inhibited tumour growth in mouse models.

Several pieces of experimental evidence suggest the biological effects of VEGF relating to angiogenesis are mediated predominantly through the KDR receptor (for review see Larrivee and Karsan, Int. J. Mol. Med., 5, 447, 2000).

The VEGF-mediated activation of KDR alone (in cell lines expressing one VEGFR-type only) was shown to be sufficient to cause cell proliferation and migration (Waltenburger et al., J. Biol. Chem., 269, 26988, 1994). Conversely, when FLT-1 alone is activated, cell proliferation is not seen and cell migration is inconsistently observed.

Experiments utilising receptor-selective VEGF mutants have shown that KDR ligation activates mitogen-activated protein kinase (MAPK) giving rise to proliferation, migration and vascular permeability (Keyt et al., J. Biol. Chem., 271, 5638, 1996). The FLT-1 selective mutant was inactive in these assays.

An anti-VEGF Mab blocking the interaction with KDR but not FLT-1 was able to inhibit VEGF-induced vascular permeability, whereas a non-blocking anti-VEGF antibody had no effect (Brekken et al., Cancer Res., 60, 5117, 2000).

The production of Mabs against the murine VEGF receptor, FLK-1, by hybridoma technology has been described (WO 94/11499). These were demonstrated to inhibit FLK-1 receptor activation by blocking the interaction of VEGF with the receptor. This inhibition of receptor activation was effective in inhibiting VEGF-induced angiogenesis in certain models. In addition, this anti-FLK-1 antibody has proven effective in treating several mouse xenograft tumours. However, not all antibodies that bind FLK-1 will bind KDR with sufficient affinity for therapeutic efficacy.

VEGF-KDR binding also inhibits apoptosis of newly formed blood vessels via the KDR-mediated activation of the PI3-kinase-Akt kinase signalling pathways (Akt kinase is a well-known downstream kinase of the PI3-kinase pathway involved in cell survival, Gerber et al., J. Biol. Chem., 273, 30336, 1998). Animal models also demonstrated the effectiveness of blockade of this anti-apoptotic response through blocking the VEGF-KDR interaction.

It is currently believed that KDR is the most important receptor in mediating the effects of VEGF and its role in promoting angiogenesis and new vessel survival appears universally acknowledged.

Therefore, an antibody molecule able to bind KDR and block its activation by VEGF may be of therapeutic benefit in the treatment of pathologies in which VEGF and/or KDR are implicated. For example, cases of inflammation, psoriasis, rheumatoid arthritis and tumour growth. There are also strong arguments that this may be best achieved through blocking its interaction with the KDR receptor. There is a need for such an antibody molecule which can be used repeatedly and produced easily and efficiently. There is also a need for an antibody molecule that has high affinity for KDR and low immunogenicity in humans.

In a first aspect, the present invention provides an antibody molecule having specificity for KDR, comprising a heavy chain wherein the variable domain comprises a CDR (as defined by Kabat et al., (supra)) having the sequence given as H1 in FIG. 1 (SEQ ID NO:1) for CDRH1, as H2 in FIG. 1 (SEQ ID NO:2) for CDRH2 or as H3 in FIG. 1 (SEQ ID NO:3) for CDRH3.

The antibody molecule of the first aspect of the present invention comprises at least one CDR selected from H1, H2 and H3 (SEQ ID NO:1 to SEQ ID NO:3) for the heavy chain variable domain. Preferably, the antibody molecule comprises at least two and more preferably all three CDRs in the heavy chain variable domain.

In a second aspect of the present invention, there is provided an antibody molecule having specificity for human KDR, comprising a light chain wherein the variable domain comprises a CDR (as defined by Kabat et al., (supra)) having the sequence given as L1 in FIG. 1 (SEQ ID NO:4) for CDRL1, as L2 in FIG. 1 (SEQ ID NO:5) for CDRL2 or as L3 in FIG. 1 (SEQ ID NO:6) for CDRL3.

The antibody molecule of the second aspect of the present invention comprises at least one CDR selected from L1, L2 and L3 (SEQ ID NO:4 to SEQ ID NO:6) for the light chain variable domain. Preferably, the antibody molecule comprises at least two and more preferably all three CDRs in the light chain variable domain.

The antibody molecules of the first and second aspects of the present invention preferably have a complementary light chain or a complementary heavy chain, respectively.

Preferably, the antibody molecule of the first or second aspect of the present invention comprises a heavy chain wherein the variable domain comprises a CDR (as defined by Kabat et al., (supra)) having the sequence given as H1 in FIG. 1 (SEQ ID NO:1) for CDRH1, as H2 in FIG. 1 (SEQ ID NO:2) for CDRH2 or as H3 in FIG. 1 (SEQ ID NO:3) for CDRH3 and a light chain wherein the variable domain comprises a CDR (as defined by Kabat et al., (supra)) having the sequence given as L1 in FIG. 1 (SEQ ID NO:4) for CDRL1, as L2 in FIG. 1 (SEQ ID NO:5) for CDRL2 or as L3 in FIG. 1 (SEQ ID NO:6) for CDRL3.

The CDRs given in SEQ ID NOS:1 to 6 (FIG. 1) referred to above are derived from a mouse monoclonal antibody VR165. The present invention also provides the mouse monoclonal antibody VR165. The sequences of the variable domains of the VR165 antibody are shown in FIG. 2 (SEQ ID NOS: 7 and 8). The light chain constant region of VR165 is kappa and the heavy chain constant region is IgG2a. This mouse antibody is referred to below as "the donor antibody".

In a second alternatively preferred embodiment, the antibody according to either of the first and second aspects of the present invention is a chimeric mouse/human antibody molecule, referred to herein as the chimeric VR165 antibody molecule. The chimeric VR165 antibody molecule comprises the variable domains of the mouse Mab VR165 (SEQ ID NOS:7 and 8) and human constant domains. Preferably, the chimeric VR165 antibody molecule comprises the human C kappa domain (Hieter et al., Cell, 22, 197-207, 1980; Genebank accession number J00241) in the light chain and the human gamma 4 domains (Flanagan et al., Nature, 300, 709-713, 1982) in the heavy chain.

In a third alternatively preferred embodiment, the antibody according to either of the first and second aspects of the present invention is a CDR-grafted antibody molecule. The term "a CDR-grafted antibody molecule" as used herein refers to an antibody molecule wherein the heavy and/or light chain contains one or more CDRs from the donor antibody (e.g. a murine Mab) grafted into a heavy and/or light chain variable region framework of an acceptor antibody (e.g. a human antibody).

Preferably, such a CDR-grafted antibody has a variable domain comprising human acceptor framework regions as well as one or more of the donor CDRs referred to above.

When the CDRs are grafted, any appropriate acceptor variable region framework sequence may be used having regard to the class/type of the donor antibody from which the CDRs are derived, including mouse, primate and human framework regions. Examples of human frameworks which can be used in the present invention are KOL, NEWM, REI, EU, TUR, TEI, LAY and POM (Kabat et al. (supra)). For example, KOL and NEWM can be used for the heavy chain, REI can be used for the light chain and EU, LAY and POM can be used for both the heavy chain and the light chain.

The preferred framework regions for the heavy chain are the human germline group 3 framework regions shown in FIG. 3 (VH3-7 GL, SEQ ID NO:9). The preferred framework regions for the light chain are the human germline sequence group 1 framework regions shown in FIG. 3 (A30 GL, SEQ ID NO:10).

In a CDR-grafted antibody of the present invention, it is preferred to use as the acceptor antibody one having chains which are homologous to the chains of the donor antibody. The acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody. Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has human germline group 3 framework regions (shown in FIG. 3) (SEQ ID NO:9), then the acceptor framework regions of the heavy chain comprise, in addition to one or more donor CDRs, donor residues at positions 77 and 93 (according to Kabat et al. (supra)).

Preferably, in a CDR-grafted antibody molecule according to the present invention, if the acceptor light chain has human group 1 framework regions (shown in FIG. 3) (SEQ ID NO:10) then the acceptor framework regions of the light chain comprise donor residues at positions 36, 44, 60, 66, 69, 70 and 71 (according to Kabat et al. (supra)).

Donor residues are residues from the donor antibody, i.e. the antibody from which the CDRs were originally derived.

The antibody molecule of the present invention may comprise: a complete antibody molecule, having full length heavy and light chains; a fragment thereof, such as a Fab, modified Fab, di-Fab, a di-(modified Fab), Fab', F(ab')₂ or Fv fragment; a light chain or heavy chain monomer or dimer; a single chain antibody, e.g. a single chain Fv in which the heavy and light chain variable domains are joined by a peptide linker. Similarly, the heavy and light chain variable regions may be combined with other antibody domains as appropriate.

Preferably the antibody molecule of the present invention is a Fab fragment. Preferably the Fab fragment has a light chain having the sequence given as SEQ ID NO:11 (FIG. 4) and a heavy chain having the sequence given as SEQ ID NO:12 (FIG. 5). The amino acid sequences given in SEQ ID NO:11 and SEQ ID NO:12 are preferably encoded by the nucleotide sequences given in SEQ ID NO:13 and SEQ ID NO:14, respectively (FIG. 4 and FIG. 5).

Alternatively, it is preferred that the antibody molecule of the present invention is a modified Fab fragment wherein the modification is the addition to the C-terminal end of its heavy chain of one or more amino acids to allow the attachment of an effector or reporter molecule. Preferably, the additional amino acids form a modified hinge region containing one or two cysteine residues to which the effector or reporter molecule may be attached. Such a modified Fab fragment preferably has a light chain having the sequence given as SEQ ID NO:11 and the heavy chain having the sequence given as SEQ ID NO:12. The amino acid sequences given in SEQ ID NO:11 and SEQ ID NO:12 are preferably encoded by the nucleotide sequences given in SEQ ID NO:13 and SEQ ID NO:14, respectively.

In a further alternative, it is particularly preferred that the antibody molecule of the present invention is a di-(modified Fab) fragment wherein the modification is the addition to the C-terminal end of each Fab heavy chain of one or more amino acids to allow the attachment of the chain to another such chain and to an effector or reporter molecule. Preferably the additional amino acids form a modified hinge region containing one, two or three cysteine residues, for attachment to the other Fab, the effector or reporter molecules.

A preferred effector group is a polymer molecule, which may be attached to the modified Fab or di-(modified Fab) fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo-or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof. "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 25000 to 40000 Da. The polymer size may in particular be selected on the basis of the intended use of the product.

Particularly preferred polymers include a polyalkylene polymer, such as a poly(ethyleneglycol) or, especially, a methoxypoly(ethyleneglycol) or a derivative thereof, and especially with a molecular weight in the range from about 25000 Da to about 40000 Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more other effector or reporter molecules attached to it. The effector or reporter molecules may be attached to the antibody fragment through any available amino acid side-chain or terminal amino acid functional group located in the fragment, for example any free amino, imino, hydroxyl or carboxyl group.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Shearwater Polymers Inc., Huntsville, Ala., USA) or may be prepared from commercially available starting materials using conventional chemical procedures.

As regards attaching poly(ethyleneglycol) (PEG) moieties, reference is made to "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York.

Where it is desired to obtain an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/06231, WO 92/22583, WO 90/09195 and WO 89/01476. Alternatively, where the effector or reporter molecule is a protein or polypeptide the linkage may be achieved using recombinant DNA procedures, for example as described in WO 86/01533 and EP-A-0392745.

Preferably, the modified Fab fragment or di-Fab of the present invention is PEGylated (i.e. has PEG (poly(ethyleneglycol)) or mPEG (methoxypoly(ethyleneglycol)) covalently attached thereto) according to the methods disclosed in EP-A-0948544 and EP-A-1090037. Preferably the antibody molecule of the present invention is a PEGylated modified Fab fragment as shown in FIG. 6 or a PEGylated di-(modified Fab) fragment. As shown in FIG. 6, the modified Fab fragment has a maleimide group covalently linked to a single thiol group in a modified hinge region. A lysine residue is covalently linked to the maleimide group. To each of the amine groups on the lysine residue is attached a methoxypoly (ethyleneglycol) polymer having a molecular weight of approximately 20,000 Da. The total molecular weight of the entire effector molecule is therefore approximately 40,000 Da. Similarly each mPEG may be linked to a lysine residue covalently attached to a bis-maleimide linker as described in EP-A-1090037 to form a PEGylated di-(modified Fab) according to the invention.

Preferably, in the compound shown in FIG. 6, the heavy chain of the antibody part has the sequence given as SEQ ID NO:12 and the light chain has the sequence given in SEQ ID NO:11.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking KDR ligation by VEGF.

Also, the antibody molecule of the present invention may have an effector or a reporter molecule attached to it. For instance, it may have a macrocycle, for chelating a heavy metal atom, or a toxin, such as ricin, attached to it by a covalent bridging structure. Alternatively, procedures of recombinant DNA technology may be used to produce an antibody molecule in which the Fc fragment (CH2, CH3 and hinge domains), the CH2 and CH3 domains or the CH3 domain of a complete immunoglobulin molecule has (have) been replaced by, or has attached thereto by peptide linkage, a functional non-immunoglobulin protein, such as an enzyme or toxin molecule.

The antibody molecule of the present invention preferably has a binding affinity of $0.4 \times 10^{-10}$ M. Preferably, the antibody molecule of the present invention comprises the heavy chain variable domain gH3 (SEQ ID NO:15) and the light chain variable domain gL3 (SEQ ID NO:16). The sequences of the variable domains of these light and heavy chains are shown in FIG. 7.

The present invention also relates to variants of the antibody molecule of the present invention, which have an improved affinity for KDR. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The present invention also provides a DNA sequence encoding the heavy and/or light chain(s) of the antibody molecule of the present invention, for example as described in the figures herein.

The DNA sequence of the present invention may comprise synthetic DNA, for instance produced by chemical processing, cDNA, genomic DNA or any combination thereof.

The present invention also relates to a cloning or expression vector comprising one or more DNA sequences of the present invention. Preferably, the cloning or expression vector comprises two DNA sequences, encoding the light chain and the heavy chain of the antibody molecule of the present invention, respectively.

In a preferred embodiment, the present invention provides an *E. coli* expression vector comprising a DNA sequence of the present invention. Preferably the expression vector is pTTOD(CDP791) as shown schematically in FIG. 8.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

DNA sequences which encode the antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecule of the present invention. Bacterial, for example *E. coli*, and other microbial systems may be used, in part, for expression of antibody fragments such as Fab, di-(modified Fab) and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule.

Preferably the process for the production of the antibody molecule of the present invention comprises culturing *E. coli* comprising an *E. coli* expression vector comprising the DNA sequence of the present invention under conditions suitable for leading to expression of protein from the DNA sequence and isolating the antibody molecule. The antibody molecule may be secreted from the cell or targeted to the periplasm by suitable signal sequences. Alternatively, the antibody molecules may accumulate within the cell's cytoplasm. Preferably the antibody molecule is targeted to the periplasm. Depending on the antibody molecule being produced and the process used, it is desirable to allow the antibody molecules to refold and adopt a functional conformation. Procedures for allowing antibody molecules to refold are well known to those skilled in the art.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The present invention also provides a therapeutic or diagnostic composition comprising an antibody molecule of the present invention in combination with a pharmaceutically acceptable excipient, diluent or carrier.

The present invention also provides a process for preparation of a therapeutic or diagnostic composition comprising admixing the antibody molecule of the present invention together with a pharmaceutically acceptable excipient, diluent or carrier.

The antibody molecule may be the sole active ingredient in the therapeutic or diagnostic composition or may be accompanied by other active ingredients including other antibody ingredients, for example anti-T cell, anti-IFNγ or anti-LPS antibodies, or non-antibody ingredients such as xanthines.

The pharmaceutical compositions should preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, an effective dose will be from 0.01 mg/kg to 50 mg/kg, preferably 0.1 mg/kg to 20 mg/kg, more preferably about 15 mg/kg.

Compositions may be administered individually to a patient or may be administered in combination with other agents, drugs or hormones.

The dose at which the antibody molecule of the present invention is administered depends on the nature of the condition to be treated, the degree to which the level of VEGF to be neutralised is, or is expected to be, raised above a desirable level, and on whether the antibody molecule is being used prophylactically or to treat an existing condition. The dose will also be selected according to the age and condition of the patient.

Thus, for example, where the product is for treatment or prophylaxis of a chronic inflammatory disease, such as rheumatoid arthritis, suitable doses of the antibody molecule of the present invention lie in the range of between 0.5 and 50 mg/kg, more preferably between 1 and 20 mg/kg and most preferably about 15 mg/kg. The frequency of dose will depend on the half-life of the antibody molecule and the duration of its effect.

If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, per week or even once every 1 or 2 months.

A pharmaceutical composition may also contain a pharmaceutically acceptable carrier for administration of the antibody. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy, In order to achieve this, DNA sequences encoding the heavy and light chains of the antibody molecule under the control of appropriate DNA componentsare introduced into a patient such that the antibody chains are expressed from the DNA sequences and assembled in situ.

The present invention also provides the antibody molecule of the present invention for use in treating a disease in which VEGF and/or KDR are implicated.

The present invention further provides the use of the antibody molecule according to the present invention in the manufacture of a medicament for the treatment of a disease in which VEGF and/or KDR are implicated.

The antibody molecule of the present invention may be utilised in any therapy where it is desired to reduce the level of biologically active KDR present in the human or animal body. The VEGF may be circulating in the body or present in an undesirably high level localised at a particular site in the body.

For example, VEGF (and therefore KDR) has been implicated in a number of pathological conditions including inflammation, psoriasis, rheumatoid arthritis and tumour growth and metastasis.

The present invention also provides a method of treating human or animal subjects suffering from or at risk of a disorder in which VEGF and/or KDR are implicated, the method comprising administering to the subject an effective amount of the antibody molecule of the present invention.

The antibody molecule of the present invention may also be used in diagnosis, for example in the in vivo diagnosis and imaging of disease states involving elevated levels of KDR.

The present invention is further described by way of illustration only in the following examples which refer to the accompanying Figures, in which:

FIG. 1 shows the CDR sequences of the heavy and light chain V-regions of the VR165 mouse monoclonal antibody gene (SEQ ID NOS 1-6).

FIG. 2 shows the protein sequence of mouse monoclonal antibody VR165 VH and VL domains (SEQ ID NO:7 and SEQ ID NO:8).

FIG. 3 shows the V-region protein sequences chosen as human germline acceptor frameworks. VH3-7 GL is a human germline VH gene (SEQ ID NO:9). A30 GL refers to the human VL germline sequence A30 gene (SEQ ID NO:10). In each case the germline sequence of framework 4 is provided by the human germline $J_H4$ and $J_K1$ respectively.

FIG. 4 shows the amino acid and nucleotide sequence of the CDP791 Fab light chain (SEQ ID NO:11 and SEQ ID NO:13).

FIG. 5 shows the amino acid and nucleotide sequence of the CDP791 Fab heavy chain (SEQ ID NO:12 and SEQ ID NO:14).

Figure 6:
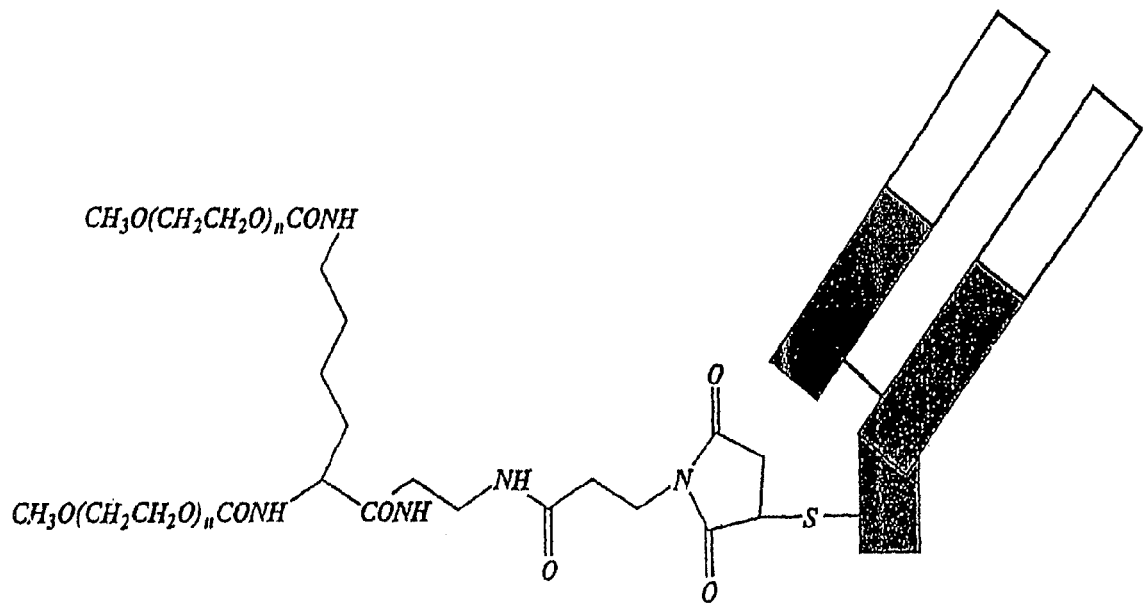

FIG. 6 shows the structure of a modified Fab fragment derived from antibody VR165 covalently linked via a cysteine residue to a lysyl-maleimide linker wherein each amino group on the lysyl residue has covalently attached to it a methoxy PEG residue wherein n is about 420;

FIG. 7 shows the protein sequences for the optimised CDR-grafted VH and VL domains gene (SEQ ID NO:15 and SEQ ID NO:16).

Figure 8:
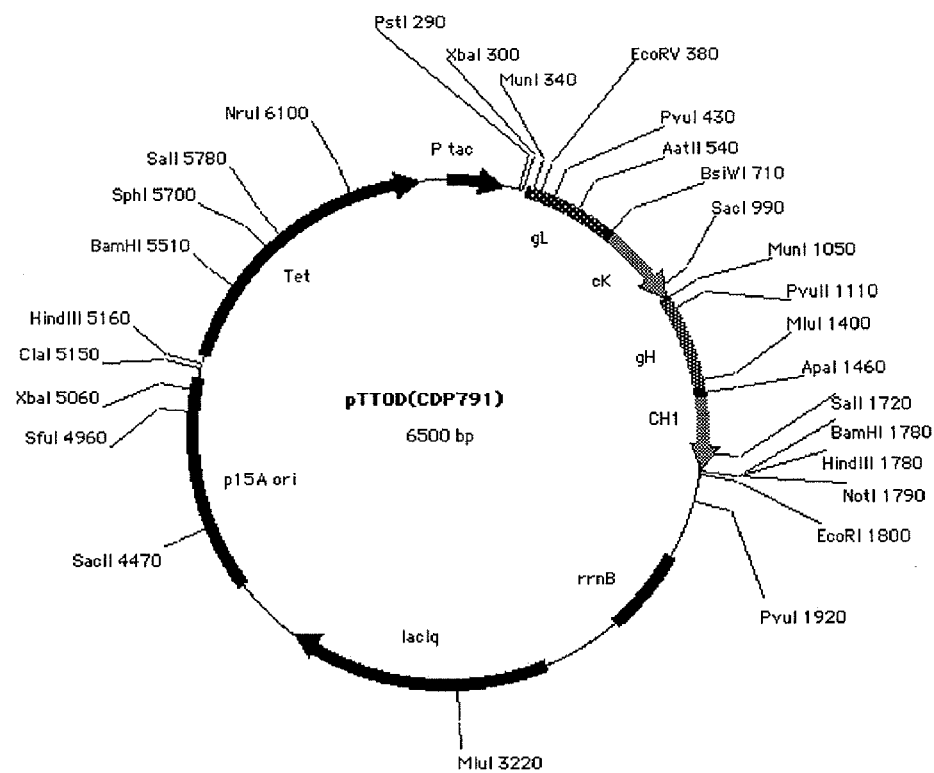

FIG. 8 shows the optimised pTTOD(CDP791) plasmid which contains the IGS-2 variant between grafts gL3 and gH3.

FIG. 9 shows the protein sequence of the designed VH and VL grafts (gH1-3 and gL1-3, SEQ ID NOS 17-22). Graft gH1 contains no murine framework residues. Graft gH2 contains murine residues at positions 77 and 93 (Kabat numbering). Both T and S are common in human germline sequences at position 77, so the inclusion of T is still consistent with a human residue. The V at position 93 is likely to be important at the VH/VL interface. The inclusion of the human residues at 60 and 62 represents the changes to the C-terminal portion of CDR-H2. Graft gL2 contains murine residues at positions 60, 66, 69, 70 and 71 (Kabat numbering). Graft gL3 contains additional murine residues at positions 36 and 44).

FIG. 10 shows the design of genes encoding the gH1 and gL1 grafts (SEQ ID NO:23 and SEQ ID NO:24).

FIG. 11 shows the oligonucleotides used to assemble the genes encoding for the gL1 and gH1 grafts (SEQ ID NOS: 25-40).

FIGS. 12a and b show plasmids pCR2.1 (gH1) and pCR2.1 (gL1) which contain the gH1 and gL1 grafts, respectively.

FIG. 13 shows oligonucleotide cassettes used in the construction of grafts gH2, 10gH3, gL2 and gL3 (SEQ ID NOS: 41-44).

FIG. 14 shows oligonucleotide pairs used in the construction of grafts gH2, gH3, gL2 and gL3 (SEQ ID NOS:45-52).

FIGS. 15a and b show plasmids pGamma4 and pNM10.1 into which the VH and VL grafts, respectively, were subcloned to enable expression in CHO cell lines.

Figure 16:
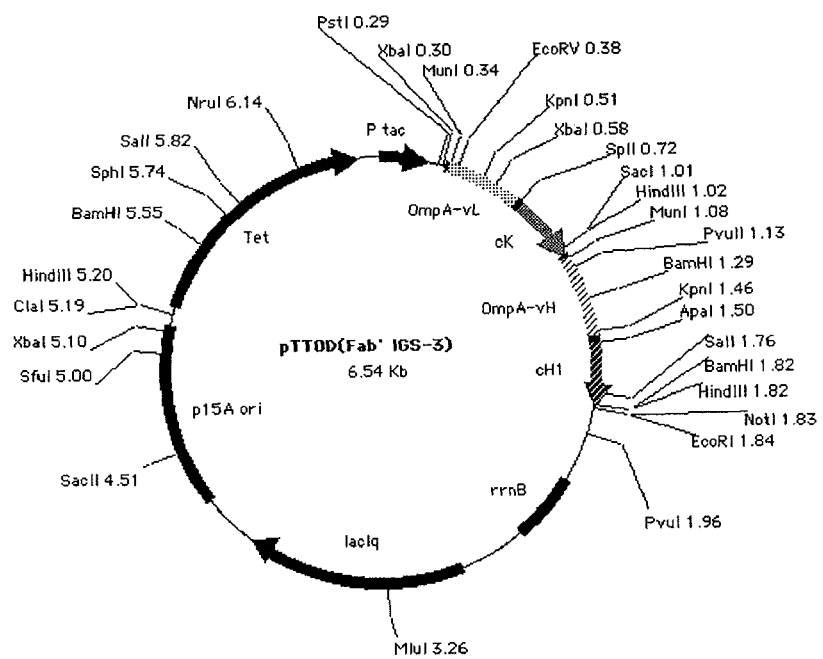

FIG. 16 shows E. coli Fab' expression plasmid pTTOD, in this case containing the IGS-3 sequence.

FIG. 17 shows the nucleotide sequence of the three IGS regions tested (SEQ ID NOS:53-55).

FIG. 18 shows the results of the Fab' fermentation comparison of IGS 20 performance.

FIG. 19 shows the coding and flanking sequence of the CDP791 Fab' fragment (SEQ ID NO:56).

FIG. 20 shows the radioimmunoassay results, in which the antibody fragments are tested for blocking of VEGF binding to KDR.

FIG. 21 shows the amino acid sequence of the entire heavy chain of the gH3-grafted VR165-derived monoclonal antibody (SEQ ID NO:57).

EXAMPLES

Monoclonal Antibody Production and Selection

An in-house immunisation program was initiated to select an antibody to human KDR that potently blocks the interaction with its ligand VEGF. Mice were immunised with a variety of immunogens including CHO cells transfected with full length human KDR, purified human KDR-human Fc fusion proteins and DNA encoding these fusion proteins. From a total of 19 fusions from animals immunised with cellular/protein immunogens, and 4 fusions from animals immunised with DNA, approximately 23,000 wells were screened in a primary ELISA format for binding to human 7-domain KDR-Fc. About 800 antibodies were then subjected to a secondary screen, a radioimmunoassay measuring blocking of 125-I VEGF binding to human 7-domain KDR-Fc. A tertiary screen measured the blocking of VEGF stimulated Tissue Factor release from human umbilical vein endothelial cells (HUVECs). From this screening cascade, antibody VR165 was selected (data not shown).

Gene Cloning of VR165

RNA was prepared from hybridoma cells expressing VR165 and was reverse transcribed to DNA. This was then used as the template for a series of PCR reactions to amplify the V-region sequences. Degenerate primer pools designed to anneal within the conserved heavy and light chain signal sequences were used as forward primers, while primers encoding the framework 4/C-region junction served as reverse primers. In this way, the V-region genes of both the heavy and light chain were amplified and then cloned and sequenced. The DNA sequences were translated to give the VR165 V-region amino acid sequence which was verified by reference to the protein sequence determined by N-terminal sequencing. The murine V-region genes were then sub-cloned into the expression vectors pMR10.1 and pGamma-4. These are separate vectors for expression of the light and heavy chain respectively containing genomic DNA encoding constant region genes for human kappa light chain and gamma-4 heavy chain. Co-transfection into CHO cells generates chimeric VR165 antibody.

Design of CDR-Grafted Sequences

VR165 was CDR-grafted onto human frameworks in order to reduce potential immunogenicity and to facilitate E. coli expression. Human germline acceptor frameworks were chosen from sub-group VHIII and VLI. The heavy chain acceptor framework is the human germline sequence VH3-7, with framework 4 coming from this portion of the human JH-region germline JH4. The light chain acceptor framework is the human germline sequence A30, with framework 4 coming from this portion of the human JKregion germline JKL The alignment shows that there are 15 framework differences between the donor and acceptor heavy chains. At each of these positions an analysis was made of the potential of that residue to contribute to antigen binding; if considered important, the murine donor residue was retained. The light chain alignment shows that there are 24 framework differences between the donor and acceptor sequences. The potential of the murine residue to contribute to antigen binding was again analysed. In this way, three VH grafts were designed and three VL grafts (FIG. 9, SEQ ID NOS:17-22).

In each case graft 1 represents a graft without murine framework residues. Grafts 2 and 3 contain murine framework residues at the positions shown. Graft gH3 also contains additional human residues at the C-terminal end of CDR-112. This portion of the CDR is not at the antigen binding surface. Genes were designed to encode the grafted sequences, using codons frequently used in E. coli genes and avoiding 'rare' E. coli eodons (Wada et al., Nucl. Acids Res., 19, 1981-86, 1991). Restriction sites were introduced into the DNA sequence at intervals to facilitate fu lier genetic manipulation. FIG. 10 shows the design of genes for gH1 and gL1 (SEQ ID NO:23 and SEQ ID NO:24). The oligonucleotides used to construct the genes are shown in FIG. 11 (SEQ ID NOS:25-40).

Construction of Genes for Grafted Sequences

A PCR assembly technique was employed to construct the CDR-grafted gH1 and gL1 V-region genes. Reaction volumes of 100 µd were set up containing 10 mM Tris-HCl pH 8.3, 1.5 mM MgCl2, 50 mM KCl, 0.001% gelatin, 0.25 mM each deoxyribonucleoside triphosphate, 1 pmole each of the 'internal' primers (F2, F3, F4, R2, R3, R4), 10 pmole each of the 'external' primers (F1, RI), and 1 unit of Taq polymerase (AmpliTaq, Applied BioSystems, catalogue no. N808-0171). PCR cycle parameters were 94° C. for 1 minute, 55° C. for 1 minute and 72° C. for 1 minute, for 30 cycles. The reaction products were then run on a 1.5% agarose gel, excised and recovered using QIAGEN spin columns (QIAquick gel extraction kit, cat no. 28706). The DNA was eluted in a volume of 30 µl. Aliquots (1 µl) of the gH1 and gL1 DNA were then cloned into the InVitrogen TOPO TA cloning vector pCR2.1 TOPO (catalogue no. K4500-01) according to the manufacturer's instructions. This non-expression vector served as a cloning intermediate to facilitate sequencing of a large number of clones. DNA sequencing using vector specific primers was used to identify correct clones containing gH1 and gL1, creating plasmids pCR2. I (gH 1), and pCR2.1 (gL 1) (see FIGS. 12a and b).

An oligonucleotide cassette replacement method was used to create the humanised grafts gH2 and gL2. FIG. 13 shows the design of the oligonucleotide cassettes (SEQ ID NO:41 and SEQ ID NO:43). To construct each variant, the vector (pCR2.1(gH1) or pCR2.1(gL1)) was cut with the restriction enzymes shown (FIG. 13, restriction sites underlined), the large vector fragment was gel purified from agarose and was used in ligation with the oligonuceotide cassette. FIG. 14 shows the sequences of the oligonucleotides used in the cassettes (SEQ ID NOS:45-46 and SEQ ID NOS:49-50). Pairs were annealed together mixing at a concentration of 0.5 pmoles/µl in a volume of 200 µl containing 12.5 mM TrisHCl pH 7.5, 2.5 mM MgCl2, 25 mM NaCl, 0.25 mM dithioerythritol, and heating to 95° C. for 3 minutes in a waterbath (volume 500 ml) then allowed to slow-cool to room temperature. The annealed oligonucleotide cassette was then diluted ten-fold in water before ligation into the appropriately cut vector. DNA sequencing was used to confirm the correct sequence, creating plasmids pCR2.1(gH2) and pCR2.I (gL2).

Variants gH3 and gL3 were constructed in similar fashion from gH2 and gL2. The cassettes and oligonucleotides are shown in FIGS. 13 and 14 (SEQ ID NO:42 and SEQ ID NO:44, SEQ ID NOS:47-48 and SEQ ID NOS:51-52). Construction of gL3 required a modified strategy because of the existence of PvuI sites in the pCR2.1 vector backbone. Cleavage of pCR2.1 (gL2) with AatII and SfuI created a vector molecule into which was ligated the PvuI-AatII annealed cassette plus a 225 base pair SfuI-PvuI fragment also prepared from pCR2.1(gL2). DNA sequencing was used to confirm the correct sequence, creating plasmids pCR2.1 (gH3) and pCR2.1 (gL3).

Each of the 3 heavy chain grafts was then sub-cloned into the expression vector pGamma-4 as HindIII-ApaI fragments. Each of the 3 light chain grafts was sub-cloned into the light chain expression vector pMRI0.1 as SfuI-BsiWI fragments. FIGS. 15a and b show maps of these expression vectors. Antibodies were expressed transiently by co transfection into CHO cells. All combinations of grafted chain and chimeric chain were expressed and compared against the double chimeric antibody.

Binding was assessed in a KDR binding ELISA, in a radio-immunoassay of inhibition of labeled VEGF binding to KDR and in a BIAcore assay of KDR binding. All the grafted forms performed well in the ELISA and radioimmunoassay, showing activity similar to the chimeric. From the BIAcore analysis, graft gL3gH3 was selected as the optimum (data not shown), and is henceforth referred to as g165.

Construction of Plasmid pTTOD

Plasmid pTTO-1 was constructed as follows.

(a) Replacement of the pTTQ9 Polylinker

Plasmid pTTQ9 was obtained from Amersham. An aliquot (2 µg) was digested with restriction enzymes SalI and EcoRI, the digest was run on a 1% agarose gel and the large DNA fragment (4520 bp) was purified. Two oligonucleotides were synthesized which, when annealed together, encode the OmpA polylinker region. This sequence has cohesive ends which are compatible with the SalI and EcoRI ends generated by restriction of pTTQ9. By cloning this oligonucleotide 'cassette' into the pTTQ9 vector, the SalI site is not regenerated, but the EcoRI site is maintained. The cassette encodes the first 13 amino acids of the signal sequence of the *E. coli* outer-membrane protein Omp-A, preceded by the Shine Dalgarno ribosome binding site of the OmpA gene. In addition restriction sites for enzymes XbaI, MunI, StyI and SplI are present. The Muni and StyI sites are within the coding region of the OmpA signal sequence and are intended as the 5' cloning sites for insertion of genes. The two oligonucleotides which make up this cassette were annealed together by mixing at a concentration of 5 pmoles/µl and heating in a waterbath to 95° C. for 3 minutes, then slow cooling to room temperature. The annealed sequence was then ligated into the SalI/EcoRI cut pTTQ9. The resulting plasmid intermediate, termed pTQOmp, was verified by DNA sequencing.

(b) Fragment Preparation and Ligation

Plasmid pTTO-1 was constructed by ligating one DNA fragment from plasmid pACYC184 to two fragments generated from pTQOmp., Plasmid pACYC184 was obtained from New England Biolabs. An aliquot (2 µg) was digested to completion with restriction enzyme StyI, then treated with Mung Bean Nuclease; this treatment creates blunt ends by cutting back 5' base overhangs. Following phenol extraction and ethanol precipitation, the DNA was restricted with enzyme PvuII, generating fragments of 2348, 1081, 412 and 403 bp. The 2348 bp fragment was purified after agarose gel electrophoresis. This fragment encodes the tetracycline resistance marker and the p15A origin of replication. The fragment was then treated with calf intestinal alkaline phosphatase to remove 5' terminal phosphates, thereby preventing the self-ligation of this molecule.

An aliquot (2 µg) of plasmid pTQOmp was digested with enzymes SspI and EcoRI, and the 2350 bp fragment was purified from unwanted fragments of 2040 bp and 170 bp following agarose gel electrophoresis; this fragment encodes the transcriptional terminator region and the lacIq gene. Another aliquot (2 µg) of pTQOmp was digested with EcoRI and XmnI, generating fragments of 2289, 1670, 350 and 250 bp. The 350 bp fragment, encoding the tac promoter, OmpA signal sequence and multicloning site, was gel purified.

The three fragments were then ligated, using approximately equimolar amounts of each fragment, to generate the plasmid pTTO-1. All cloning junctions were verified by DNA sequencing.

(c) Production of Plasmid pTTOD

Plasmid pTTOD was derived from pTTO-1 by removal of backbone restriction sites for PvuII (3 sites), EcoRV (2 sites) and ApaI (1 site). These changes were made to simplify Fab' coding strategies. In making these changes the coding protein sequence of the lacIq gene and tetracycline resistance gene were not altered, although 'silent' changes were made at the DNA level. A PCR strategy was used, in which primers bearing 'silent' changes which removed these restriction sites were designed and used to amplify sections of the parent plasmid (pTTO-1). Flanking restriction sites (unaltered) were then used to replace sequences in the parent plasmid with these modified sequences. By this multi-stage process plasmid pTTOD was created. Transfer of existing Fab' genes within vector pTTO into pTTOD was achieved using the unique PstI and EcoM sites which flank the genes, creating pTTOD(Fab').

Insertion of g165 V-Region Genes into *E. coli* Fab' Expression Plasmid pTTOD

The starting point for insertion of g165 sequences was 3 vectors for expression of an irrelevant Fab', pTTOD(Fab' IGS-1), pTTOD(Fab' IGS-2) and pTTOD(Fab' IGS-3) (for example, see FIG. 16). These differ only in the so-called IGS or intergenic sequence which separates the light chain gene from the heavy chain gene. These IGS regions are shown in FIG. 17 (SEQ ID NOS:53-55). Cloning of the g165 sequences into these vectors was performed as a 2-stage process. First the light chain was restricted from pCR2.1 (gL3) as a EcoRV-BsiWI fragment (395 bp) and inserted into the large vector fragment from EcoRV-BsiWI digestion of pTTOD(Fab' IGS-1), pTTOD(Fab' IGS-2) and pTTOD(Fab' IGS-3). This created the cloning intermediates pTTOD (g165L IGS-1), pTTOD(g165L IGS-2) and pTTOD(g165L IGS-3). These cloning intermediates were then cut with PvuH and ApaI, the large vector fragment was purified and the 435 by PvuII-ApaI fragment from pCR2.1(gH3) was inserted.

This created the 3 Fab' expression plasmids pTTOD(g165 IGS-1), pTTOD(g165 IGS-2) and pTTOD(g165 IGS-3).

These plasmids were transformed into the host strain W3110 and expression of Fab' by these 3 plasmids was compared in shake flasks and in the fermenter. FIG. 18 shows the results of a fermenter comparison, clearly demonstrating the superior performance of the IGS-2 variant.

Plasmid pTTOD(g165 IGS-2) was retermed pTTOD (CDP791). The plasmid map of this construct is shown in FIG. 8. FIG. 19 shows the fall DNA and protein sequence of the coding region of the Fab' in this vector, plus some of the 5' and 3' flanking sequence (SEQ ID NO:56).

PEGylation of CDR-Grafted, VR165-Based Modified Fab

The purified modified Fab is site-specifically conjugated with a branched molecule of mPEG. This is achieved by activation of a single cysteine residue in a truncated hinge region of the modified Fab, followed by reaction with (mPEG)-lysyl maleimide as previously described (A. P. Chapman et al., Nature Biotechnology 17, 780-783, 1999). The PEGylated molecule is shown in FIG. 6. Alternatively, reaction of the activated Fab with (mPEG)-lysyl bis-maleimide as described in EP-A-1090037 yields a PEGylated di-(modified Fab), hereinafter referred to as DFM.

BIAcore Activities of Naked and PEGylated Fragments

7 Ig-domain human KDR fused to human Fc was captured on a chip coated with anti-Fc, and the various fragments of the CDR grafted antibody g165 and the murine parent antibody VR165 were passed over permitting affinity determination. The table below summarises the results obtained. In this assay format, there is an advantage of divalency as shown by the lower off rates ($K_d$) of the divalent species. The affinity of the grafted DFM is very similar to the murine IgG, with the DFM-PEG showing a minor reduction of affinity. The KD of the g165 DFM-PEG molecule is approximately $4 \times 10^{-11}$ M in this assay.

TABLE 1

BIAcore activities of naked and PEGylated fragments

| a-KDR | $K_a e^5$ | $K_d e^{-4}$ | $K_D e^{-10}$ |
|---|---|---|---|
| DFM | 21.6 | 0.64 | 0.29 |
| DFM-PEG40 | 15.5 | 0.64 | 0.41 |
| mIgG | 19.8 | 0.60 | 0.30 |
| FAB | 13.6 | 12.4 | 9.1 |
| FAB-PEG40 | 11.0 | 11.8 | 10.7 |

Radioimmunoassay

The ability of the fragments to block VEGF binding to KDR was measured in a radioimmunoassay. Polyclonal anti Fc was used to capture 71 g-domain KDR fused to human Fc in a microtitre plate, antibody or fragment was added followed by 125-I labeled VEGF-165. Results of this assay are shown in FIG. 20. Again in this assay set-up there is an advantage of divalency, demonstrated by the superior blocking performance of the DFM over the Fab'. The DFM-PEG construct shows a minor reduction of activity compared to the naked DFM, as was seen in the BIAcore study.

Cell Based Assays

The molecule g164 DFM PEG also demonstrated activity in cell based assays. Its ability to block VEGF stimulation of KDR was demonstrated via inhibition of tissue factor release by human umbilical vein endothelial cells (see Clauss et al., J. Biol. Chem., 271, 17629-17634, 1996). Activity was also demonstrated via inhibition of VEGF mediated $Ca^{2+}$ mobilisation in human microvascular endothelial cells (see Cunningham et al., Am. J. Physiol., 276, C176-181, 1999).

It should be understood that the above-described examples are merely exemplary and do not limit the scope of the present invention as defined in the following claims.

SEQUENCE LISTING

<160> NUMBER OF SEQ ID NOS: 71

<210> SEQ ID NO 1
<211> LENGTH: 5
<212> TYPE: PRT
<213> ORGANISM: Mus musculus

<400> SEQUENCE: 1

Ser Tyr Gly Met Ser
1               5

<210> SEQ ID NO 2
<211> LENGTH: 17
<212> TYPE: PRT
<213> ORGANISM: Mus musculus

<400> SEQUENCE: 2

Thr Ile Thr Ser Gly Gly Ser Tyr Thr Tyr Tyr Pro Asp Thr Val Lys
1               5                   10                  15

Gly

<210> SEQ ID NO 3
<211> LENGTH: 8
<212> TYPE: PRT
<213> ORGANISM: Mus musculus

<400> SEQUENCE: 3

Ile Gly Glu Asp Ala Leu Asp Tyr
1               5

<210> SEQ ID NO 4
<211> LENGTH: 11
<212> TYPE: PRT
<213> ORGANISM: Mus musculus

<400> SEQUENCE: 4

Arg Ala Ser Gln Asp Ile Ala Gly Ser Leu Asn
1               5                   10

<210> SEQ ID NO 5
<211> LENGTH: 7
<212> TYPE: PRT
<213> ORGANISM: Mus musculus

<400> SEQUENCE: 5

Ala Thr Ser Ser Leu Asp Ser
1               5

<210> SEQ ID NO 6
<211> LENGTH: 9
<212> TYPE: PRT
<213> ORGANISM: Mus musculus

<400> SEQUENCE: 6

Leu Gln Tyr Gly Ser Phe Pro Pro Thr
1               5

<210> SEQ ID NO 7
<211> LENGTH: 117
<212> TYPE: PRT
<213> ORGANISM: Mus musculus

<400> SEQUENCE: 7

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Gln Trp Val
        35                  40                  45

Ala Thr Ile Thr Ser Gly Gly Ser Tyr Thr Tyr Tyr Pro Asp Thr Val
    50                  55                  60

Lys Gly Arg Phe Thr Ile Ser Arg Asp Asn Ala Glu Asn Thr Leu Tyr
65                  70                  75                  80

Leu Gln Met Ser Ser Leu Lys Ser Glu Asp Thr Ala Met Tyr Tyr Cys
                85                  90                  95

Val Arg Ile Gly Glu Asp Ala Leu Asp Tyr Trp Gly Gln Gly Thr Ser
            100                 105                 110

Val Thr Val Ser Ser
        115

<210> SEQ ID NO 8
<211> LENGTH: 108
<212> TYPE: PRT
<213> ORGANISM: Mus musculus

<400> SEQUENCE: 8

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Ala Gly Ser
            20                  25                  30

Leu Asn Trp Leu Arg Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Gly Ser Phe Pro Pro
                85                  90                  95

Thr Phe Gly Gly Gly Ser Lys Leu Glu Ile Lys Arg
            100                 105
```

<210> SEQ ID NO 9
<211> LENGTH: 109
<212> TYPE: PRT
<213> ORGANISM: Homo sapiens
<220> FEATURE:
<221> NAME/KEY: VH3-7 GL V-region

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105
```

<210> SEQ ID NO 10
<211> LENGTH: 106
<212> TYPE: PRT
<213> ORGANISM: Homo sapiens
<220> FEATURE:
<221> NAME/KEY: A30 GL V-region

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95
```

Gly Gln Gly Thr Lys Val Glu Ile Lys Arg
            100                 105

<210> SEQ ID NO 11
<211> LENGTH: 235
<212> TYPE: PRT
<213> ORGANISM: Artificial Sequence
<220> FEATURE:
<223> OTHER INFORMATION: CDP791 Fab' light chain

<400> SEQUENCE: 11

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ala Gly Ser Leu Asn Trp Leu Gln Gln Lys Pro Gly Lys Ala
    50                  55                  60

Ile Lys Arg Leu Ile Tyr Ala Thr Ser Ser Leu Asp Ser Gly Val Pro
65                  70                  75                  80

Lys Arg Phe Ser Gly Ser Arg Ser Gly Ser Asp Tyr Thr Leu Thr Ile
                85                  90                  95

Ser Ser Leu Gln Pro Glu Asp Phe Ala Thr Tyr Tyr Cys Leu Gln Tyr
            100                 105                 110

Gly Ser Phe Pro Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 12
<211> LENGTH: 248
<212> TYPE: PRT
<213> ORGANISM: Artificial Sequence
<220> FEATURE:
<223> OTHER INFORMATION: CDP791 Fab' heavy chain

<400> SEQUENCE: 12

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Gly Met Ser Trp Val Arg Gln Ala Pro Gly Lys

```
                  50                  55                  60
Gly Leu Glu Trp Val Ala Thr Ile Thr Ser Gly Gly Ser Tyr Thr Tyr
 65                      70                  75                  80

Tyr Val Asp Ser Val Lys Gly Arg Phe Thr Ile Ser Arg Asp Asn Ala
                         85                  90                  95

Lys Asn Thr Leu Tyr Leu Gln Met Asn Ser Leu Arg Ala Glu Asp Thr
                    100                 105                 110

Ala Val Tyr Tyr Cys Val Arg Ile Gly Glu Asp Ala Leu Asp Tyr Trp
                115                 120                 125

Gly Gln Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Leu Gly Thr Gln Thr Tyr Ile Cys Asn Val Asn His
                210                 215                 220

Lys Pro Ser Asn Thr Lys Val Asp Lys Lys Val Glu Pro Lys Ser Cys
225                 230                 235                 240

Asp Lys Thr His Thr Cys Ala Ala
                245
```

<210> SEQ ID NO 13
<211> LENGTH: 708
<212> TYPE: DNA
<213> ORGANISM: Artificial Sequence
<220> FEATURE:
<223> OTHER INFORMATION: CDP791 Fab' light chain

<400> SEQUENCE: 13

```
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgtgccag tcaggacatc gcgggtagcc tgaactggtt gcagcaaaaa     180
ccgggcaaag ccatcaagcg cctcatctat gcgacgtcca gcctggatag cggtgtgcca     240
aaacgtttca gtggcagtcg cagcggttct gactataccc tcacaatttc gtctctccag     300
ccggaagatt tcgccactta ctattgtctg caatatggca gcttccctcc gaccttcggt     360
cagggcacta aagtagaaat caaacgtacg gtagcggccc catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag acagcaccct acagcctcag cagcaccctg     600
acgctgagca aagcagacta cgagaaacac aaagtctacg cctgcgaagt cacccatcag     660
ggcctgagct caccagtaac aaaaagtttt aatagagggg agtgttaa                  708
```

<210> SEQ ID NO 14
<211> LENGTH: 750
<212> TYPE: DNA
<213> ORGANISM: Artificial Sequence
<220> FEATURE:
<223> OTHER INFORMATION: CDP791 Fab' heavy chain

<400> SEQUENCE: 14

```
atgaagaaga ctgctatagc aattgcagtg gcgctagctg gtttcgccac cgtggcgcaa    60
gctgaggttc agctggtcga gtctggaggc gggcttgtcc agcctggagg gagcctgcgt   120
ctctcttgtg cagcaagcgg cttcaccttt tcctcttacg gtatgtcctg ggtgcggcag   180
gcacctggga agggcctgga gtgggtggca accattacgt ccggaggcag ctatacatac   240
tacgtggaca gcgtcaaggg ccgtttcacc atttcccggg acaatgcaaa gaataccctt   300
tacctccaga tgaactctct ccgcgcagag gacacagcag tctattactg tgtacggatc   360
ggcgaagacg cgttggacta ctggggacag gggacccttg tgacagtctc ctctgcttct   420
acaaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc    660
tgcaacgtga atcacaagcc cagcaacacc aaggtcgaca agaaagttga gcccaaatct   720
tgtgacaaaa ctcacacatg cgccgcgtga                                    750
```

<210> SEQ ID NO 15
<211> LENGTH: 117
<212> TYPE: PRT
<213> ORGANISM: Artificial Sequence
<220> FEATURE:
<223> OTHER INFORMATION: Amino acid sequence of CDR-grafted VH domain

<400> SEQUENCE: 15

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ser Tyr Thr Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Ile Gly Glu Asp Ala Leu Asp Tyr Trp Gly Gln Gly Thr Leu
            100                 105                 110

Val Thr Val Ser Ser
        115
```

<210> SEQ ID NO 16
<211> LENGTH: 108
<212> TYPE: PRT
<213> ORGANISM: Artificial Sequence
<220> FEATURE:
<223> OTHER INFORMATION: Amino acid sequence of CDR-grafted VL domain

<400> SEQUENCE: 16

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ala Gly Ser
            20                  25                  30
```

```
Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Lys Arg Phe Ser Gly
 50                  55                  60

Ser Arg Ser Gly Ser Asp Tyr Thr Leu Thr Ile Ser Ser Leu Gln Pro
 65                  70                  75                  80

Glu Asp Phe Ala Thr Tyr Tyr Cys Leu Gln Tyr Gly Ser Phe Pro Pro
                 85                  90                  95

Thr Phe Gly Gln Gly Thr Lys Val Glu Ile Lys Arg
            100                 105

<210> SEQ ID NO 17
<211> LENGTH: 117
<212> TYPE: PRT
<213> ORGANISM: Artificial Sequence
<220> FEATURE:
<223> OTHER INFORMATION: gH1 VH graft

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ser Tyr Thr Tyr Tyr Pro Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ile Gly Glu Asp Ala Leu Asp Tyr Trp Gly Gln Gly Thr Leu
            100                 105                 110

Val Thr Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: gH2 VH graft

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ser Tyr Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Ile Gly Glu Asp Ala Leu Asp Tyr Trp Gly Gln Gly Thr Leu
            100                 105                 110
```

```
Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: gH3 VH graft

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ser Tyr Thr Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Ile Gly Glu Asp Ala Leu Asp Tyr Trp Gly Gln Gly Thr Leu
            100                 105                 110

Val Thr Val Ser Ser
        115

<210> SEQ ID NO 20
<211> LENGTH: 108
<212> TYPE: PRT
<213> ORGANISM: Artificial Sequence
<220> FEATURE:
<223> OTHER INFORMATION: gL1 VL graft

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ala Gly Ser
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Gly Ser Phe Pro Pro
                85                  90                  95

Thr Phe Gly Gln Gly Thr Lys Val Glu Ile Lys Arg
            100                 105

<210> SEQ ID NO 21
<211> LENGTH: 108
<212> TYPE: PRT
<213> ORGANISM: Artificial Sequence
<220> FEATURE:
<223> OTHER INFORMATION: gL2 VL graft

<400> SEQUENCE: 21
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ala Gly Ser
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Lys Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Gly Ser Phe Pro Pro
                85                  90                  95

Thr Phe Gly Gln Gly Thr Lys Val Glu Ile Lys Arg
            100                 105
```

```
<210> SEQ ID NO 22
<211> LENGTH: 108
<212> TYPE: PRT
<213> ORGANISM: Artificial Sequence
<220> FEATURE:
<223> OTHER INFORMATION: gL3 VL graft

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ala Gly Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Lys Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Gly Ser Phe Pro Pro
                85                  90                  95

Thr Phe Gly Gln Gly Thr Lys Val Glu Ile Lys Arg
            100                 105
```

```
<210> SEQ ID NO 23
<211> LENGTH: 452
<212> TYPE: DNA
<213> ORGANISM: Artificial Sequence
<220> FEATURE:
<223> OTHER INFORMATION: Nucleotide sequence encoding the gH1 graft

<400> SEQUENCE: 23
gaataaaagc ttgccgccac catgaagatg tggttaaact gggttttcct tgccctcatt      60
ttaaaaggtg tccagtgtga ggtgcagctg gtcgagtctg gaggcgggct tgtccagcct     120
ggagggagcc tgcgtctctc ttgtgcagca agcggcttca ccttttcctc ttacggtatg     180
tcctgggtgc ggcaggcacc tgggaagggc ctggagtggg tggcaaccat tacgtccgga     240
ggcagctata catactaccc ggacaccgtc aagggccgtt tcaccatttc ccgggacaat     300
gcaaagaata gcctttacct ccagatgaac tctctccgcg cagaggacac agcagtctat     360
tactgtgcac ggatcggcga agacgcgttg gactactggg gacaggggac ccttgtgaca     420
gtctcctctg cttctacaaa gggcccaaga aa                                   452
```

<210> SEQ ID NO 24
<211> LENGTH: 414
<212> TYPE: DNA
<213> ORGANISM: Artificial Sequence
<220> FEATURE:
<223> OTHER INFORMATION: Nucleotide sequence encoding the gL1 graft

<400> SEQUENCE: 24

```
ggatgattcg aagccgccac catgaggacc cctgctcaga ttcttggctt cttgttgctc      60
ttgtttccag gtaccagatg tgatatccag atgacccaga gtccaagcag tctctccgcc     120
agcgtaggcg atcgtgtgac tattacctgt cgtgccagtc aggacatcgc gggtagcctg     180
aactggtatc agcaaaaacc gggcaaagcc cccaagcgcc tcatctatgc gacgtccagc     240
ctggatagcg gtgtgccatc tcgtttcagt ggcagtggca gcggtactga atttaccctc     300
acaatttcgt ctctccagcc ggaagatttc gccacttact attgtctgca atatggcagc     360
ttccctccga ccttcggtca gggcactaaa gtagaaatca aacgtacggc gtgc           414
```

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide used for graft construction

<400> SEQUENCE: 25

```
ggatgattcg aagccgccac                                                  20
```

<210> SEQ ID NO 26
<211> LENGTH: 86
<212> TYPE: DNA
<213> ORGANISM: Artificial Sequence
<220> FEATURE:
<223> OTHER INFORMATION: Oligonucleotide used for graft construction

<400> SEQUENCE: 26

```
tccaggtacc agatgtgata tccagatgac ccagagtcca agcagtctct ccgccagcgt      60
aggcgatcgt gtgactatta cctgtc                                           86
```

<210> SEQ ID NO 27
<211> LENGTH: 87
<212> TYPE: DNA
<213> ORGANISM: Artificial Sequence
<220> FEATURE:
<223> OTHER INFORMATION: Oligonucleotide used for graft construction

<400> SEQUENCE: 27

```
caaaaaccgg gcaaagcccc caagcgcctc atctatgcga cgtccagcct ggatagcggt      60
gtgccatctc gtttcagtgg cagtggc                                          87
```

<210> SEQ ID NO 28
<211> LENGTH: 91
<212> TYPE: DNA
<213> ORGANISM: Artificial Sequence
<220> FEATURE:
<223> OTHER INFORMATION: Oligonucleotide used for graft construction

<400> SEQUENCE: 28

```
agatttcgcc acttactatt gtctgcaata tggcagcttc cctccgacct tcggtcaggg      60
cactaaagta gaaatcaaac gtacggcgtg c                                     91
```

<210> SEQ ID NO 29

```
<211> LENGTH: 21
<212> TYPE: DNA
<213> ORGANISM: Artificial Sequence
<220> FEATURE:
<223> OTHER INFORMATION: Oligonucleotide used for graft construction

<400> SEQUENCE: 29
gcacgccgta cgtttgattt c                                              21

<210> SEQ ID NO 30
<211> LENGTH: 87
<212> TYPE: DNA
<213> ORGANISM: Artificial Sequence
<220> FEATURE:
<223> OTHER INFORMATION: Oligonucleotide used for graft construction

<400> SEQUENCE: 30
gacaatagta agtggcgaaa tcttccggct ggagagacga aattgtgagg gtaaattcag    60
taccgctgcc actgccactg aaacgag                                        87

<210> SEQ ID NO 31
<211> LENGTH: 83
<212> TYPE: DNA
<213> ORGANISM: Artificial Sequence
<220> FEATURE:
<223> OTHER INFORMATION: Oligonucleotide used for graft construction

<400> SEQUENCE: 31
ggggctttgc ccggtttttg ctgataccag ttcaggctac ccgcgatgtc ctgactggca    60
cgacaggtaa tagtcacacg atc                                            83

<210> SEQ ID NO 32
<211> LENGTH: 87
<212> TYPE: DNA
<213> ORGANISM: Artificial Sequence
<220> FEATURE:
<223> OTHER INFORMATION: Oligonucleotide used for graft construction

<400> SEQUENCE: 32
gatatcacat ctggtacctg gaaacaagag caacaagaag ccaagaatct gagcaggggt    60
cctcatggtg gcggcttcga atcatcc                                        87

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide used for graft construction

<400> SEQUENCE: 33
gaataaaagc ttgccgccac c                                              21

<210> SEQ ID NO 34
<211> LENGTH: 91
<212> TYPE: DNA
<213> ORGANISM: Artificial Sequence
<220> FEATURE:
<223> OTHER INFORMATION: Oligonucleotide used for graft construction

<400> SEQUENCE: 34
tccagtgtga ggtgcagctg gtcgagtctg gaggcgggct tgtccagcct ggagggagcc    60
tgcgtctctc ttgtgcagca agcggcttca c                                   91
```

-continued

<210> SEQ ID NO 35
<211> LENGTH: 90
<212> TYPE: DNA
<213> ORGANISM: Oligonucleotide used for graft construction

<400> SEQUENCE: 35
agtgggtggc aaccattacg tccggaggca gctatacata ctacccggac accgtcaagg    60
gccgtttcac catttcccgg gacaatgcaa                                     90

<210> SEQ ID NO 36
<211> LENGTH: 96
<212> TYPE: DNA
<213> ORGANISM: Artificial Sequence
<220> FEATURE:
<223> OTHER INFORMATION: Oligonucleotide used for graft construction

<400> SEQUENCE: 36
ctattactgt gcacggatcg gcgaagacgc gttggactac tggggacagg ggacccttgt    60
gacagtctcc tctgcttcta caaagggccc aagaaa                              96

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide used for graft construction

<400> SEQUENCE: 37
tttcttgggc cctttgtaga ag                                             22

<210> SEQ ID NO 38
<211> LENGTH: 94
<212> TYPE: DNA
<213> ORGANISM: Artificial Sequence
<220> FEATURE:
<223> OTHER INFORMATION: Oligonucleotide used for graft construction

<400> SEQUENCE: 38
ccgatccgtg cacagtaata gactgctgtg tcctctgcgc ggagagagtt catctggagg    60
taaaggctat tctttgcatt gtcccgggaa atgg                                94

<210> SEQ ID NO 39
<211> LENGTH: 94
<212> TYPE: DNA
<213> ORGANISM: Artificial Sequence
<220> FEATURE:
<223> OTHER INFORMATION: Oligonucleotide used for graft construction

<400> SEQUENCE: 39
acgtaatggt tgccacccac tccaggccct tccaggtgc ctgccgcacc caggacatac     60
cgtaagagga aaggtgaag ccgcttgctg caca                                 94

<210> SEQ ID NO 40
<211> LENGTH: 90
<212> TYPE: DNA
<213> ORGANISM: Artificial Sequence
<220> FEATURE:
<223> OTHER INFORMATION: Oligonucleotide used for graft construction

<400> SEQUENCE: 40
cagctgcacc tcacactgga cacctttaa aatgagggca aggaaaaccc agtttaacca     60
catcttcatg gtggcggcaa gcttttattc                                     90

```
<210> SEQ ID NO 41
<211> LENGTH: 102
<212> TYPE: DNA
<213> ORGANISM: Artificial Sequence
<220> FEATURE:
<223> OTHER INFORMATION: Oligonucleotide cassette for construction of
      gH2

<400> SEQUENCE: 41
tcccgggaca atgcaaagaa tacccttttac ctccagatga actctctccg cgcagaggac      60
acagcagtct attactgtgt acggatcggc gaagacgcgt tg                        102

<210> SEQ ID NO 42
<211> LENGTH: 63
<212> TYPE: DNA
<213> ORGANISM: Artificial Sequence
<220> FEATURE:
<223> OTHER INFORMATION: Oligonucleotide cassette for construction of
      gH3

<400> SEQUENCE: 42
tccggaggca gctatacata ctacgtggac agcgtcaagg gccgtttcac catttcccgg      60
gac                                                                    63

<210> SEQ ID NO 43
<211> LENGTH: 90
<212> TYPE: DNA
<213> ORGANISM: Artificial Sequence
<220> FEATURE:
<223> OTHER INFORMATION: Oligonucleotide cassette for construction of
      gL2

<400> SEQUENCE: 43
gcgacgtcca gcctggatag cggtgtgcca aaacgtttca gtggcagtcg cagcggttct      60
gactataccc tcacaatttc gtctctccag                                       90

<210> SEQ ID NO 44
<211> LENGTH: 111
<212> TYPE: DNA
<213> ORGANISM: Artificial Sequence
<220> FEATURE:
<223> OTHER INFORMATION: Oligonucleotide cassette for construction of
      gL3

<400> SEQUENCE: 44
ggcgatcgtg tgactattac ctgtcgtgcc agtcaggaca tcgcgggtag cctgaactgg      60
ttgcagcaaa aaccgggcaa agccatcaag cgcctcatct atgcgacgtc c              111

<210> SEQ ID NO 45
<211> LENGTH: 93
<212> TYPE: DNA
<213> ORGANISM: Artificial Sequence
<220> FEATURE:
<223> OTHER INFORMATION: Oligonucleotide used for cassette construction

<400> SEQUENCE: 45
ccgggacaat gcaaagaata ccctttacct ccagatgaac tctctccgcg cagaggacac      60
agcagtctat tactgtgtac ggatcggcga aga                                   93

<210> SEQ ID NO 46
<211> LENGTH: 93
<212> TYPE: DNA
<213> ORGANISM: Artificial Sequence
```

```
<220> FEATURE:
<223> OTHER INFORMATION: Oligonucleotide used for cassette construction

<400> SEQUENCE: 46
cgcgtcttcg ccgatccgta cacagtaata gactgctgtg tcctctgcgc ggagagagtt      60
catctggagg taaagggtat tctttgcatt gtc                                   93

<210> SEQ ID NO 47
<211> LENGTH: 55
<212> TYPE: DNA
<213> ORGANISM: Artificial Sequence
<220> FEATURE:
<223> OTHER INFORMATION: Oligonucleotide used for cassette construction

<400> SEQUENCE: 47
ccggaggcag ctatacatac tacgtggaca gcgtcaaggg ccgtttcacc atttc            55

<210> SEQ ID NO 48
<211> LENGTH: 55
<212> TYPE: DNA
<213> ORGANISM: Artificial Sequence
<220> FEATURE:
<223> OTHER INFORMATION: Oligonucleotide used for cassette construction

<400> SEQUENCE: 48
ccgggaaatg gtgaaacggc ccttgacgct gtccacgtag tatgtatagc tgcct            55

<210> SEQ ID NO 49
<211> LENGTH: 79
<212> TYPE: DNA
<213> ORGANISM: Artificial Sequence
<220> FEATURE:
<223> OTHER INFORMATION: Oligonucleotide used for cassette construction

<400> SEQUENCE: 49
ccagcctgga tagcggtgtg ccaaaacgtt tcagtggcag tcgcagcggt tctgactata      60
ccctcacaat ttcgtctct                                                   79

<210> SEQ ID NO 50
<211> LENGTH: 87
<212> TYPE: DNA
<213> ORGANISM: Artificial Sequence
<220> FEATURE:
<223> OTHER INFORMATION: Oligonucleotide used for cassette construction

<400> SEQUENCE: 50
ctggagagac gaaattgtga gggtatagtc agaaccgctg cgactgccac tgaaacgttt      60
tggcacaccg ctatccaggc tggacgt                                          87

<210> SEQ ID NO 51
<211> LENGTH: 103
<212> TYPE: DNA
<213> ORGANISM: Artificial Sequence
<220> FEATURE:
<223> OTHER INFORMATION: Oligonucleotide used for cassette construction

<400> SEQUENCE: 51
cgtgtgacta ttacctgtcg tgccagtcag gacatcgcgg gtagcctgaa ctggttgcag      60
caaaaaccgg gcaaagccat caagcgcctc atctatgcga cgt                       103

<210> SEQ ID NO 52
<211> LENGTH: 101
<212> TYPE: DNA
```

<213> ORGANISM: Artificial Sequence
<220> FEATURE:
<223> OTHER INFORMATION: Oligonucleotide used for cassette construction

<400> SEQUENCE: 52

```
cgcatagatg aggcgcttga tggctttgcc cggttttttgc tgcaaccagt tcaggctacc    60
cgcgatgtcc tgactggcac gacaggtaat agtcacacga t                       101
```

<210> SEQ ID NO 53
<211> LENGTH: 67
<212> TYPE: DNA
<213> ORGANISM: Artificial Sequence
<220> FEATURE:
<223> OTHER INFORMATION: IGS-1 sequence

<400> SEQUENCE: 53

```
gagctcacca gtaacaaaaa gttttaatag aggagagtgt taatgaagaa gactgctata    60
gcaattg                                                              67
```

<210> SEQ ID NO 54
<211> LENGTH: 69
<212> TYPE: DNA
<213> ORGANISM: Artificial Sequence
<220> FEATURE:
<223> OTHER INFORMATION: IGS-2 sequence

<400> SEQUENCE: 54

```
gagctcacca gtaacaaaaa gttttaatag aggggagtgt taaaatgaag aagactgcta    60
tagcaattg                                                            69
```

<210> SEQ ID NO 55
<211> LENGTH: 81
<212> TYPE: DNA
<213> ORGANISM: Artificial Sequence
<220> FEATURE:
<223> OTHER INFORMATION: IGS-3 sequence

<400> SEQUENCE: 55

```
gagctcacca gtaacaaaaa gctttaatag aggagagtgt tgaggaggaa aaaaaaatga    60
agaaaactgc tatagcaatt g                                              81
```

<210> SEQ ID NO 56
<211> LENGTH: 2000
<212> TYPE: DNA
<213> ORGANISM: Artificial Sequence
<220> FEATURE:
<223> OTHER INFORMATION: Coding and flanking sequence of CDP791 Fab'

<400> SEQUENCE: 56

```
aattctcatg tttgacagct tatcatcgac tgcacggtgc accaatgctt ctggcgtcag    60
gcagccatcg gaagctgtgg tatggctgtg caggtcgtaa atcactgcat aattcgtgtc   120
gctcaaggcg cactcccgtt ctggataatg ttttttgcgc cgacatcata acggttctgg   180
caaatattct gaaatgagct gttgacaatt aatcatcggc tcgtataatg tgtggaattg   240
tgagcggata caatttcac acaggaaaca gcgatgagct ggctgcagg tcgagttcta   300 gataacgagg cgtaaaaaat gaaaagaca gctatcgcaa ttgcagtggc cttggctggt   360
ttcgctaccg tagcgcaagc tgatatccag atgacccaga gtccaagcag tctctccgcc   420
agcgtaggcg atcgtgtgac tattacctgt cgtgccagtc aggacatcgc gggtagcctg   480
aactggttgc agcaaaaacc gggcaaagcc atcaagcgcc tcatctatgc gacgtccagc   540
```

```
ctggatagcg gtgtgccaaa acgtttcagt ggcagtcgca gcggttctga ctatacctc     600 acaatttcgt ctctccagcc ggaagatttc gccacttact attgtctgca atatggcagc    660
ttccctccga ccttcggtca gggcactaaa gtagaaatca acgtacggt agcggcccca    720 tctgtcttca tcttcccgcc atctgatgag cagttgaaat ctggaactgc ctctgttgtg    780
tgcctgctga taacttcta tcccagagag gccaaagtac agtggaaggt ggataacgcc    840
ctccaatcgg gtaactccca ggagagtgtc acagagcagg acagcaagga cagcacctac    900
agcctcagca gcaccctgac gctgagcaaa gcagactacg agaaacacaa agtctacgcc    960
tgcgaagtca cccatcaggg cctgagctca ccagtaacaa aaagttttaa tagaggggag   1020
tgttaaaatg aagaagactg ctatagcaat tgcagtggcg ctagctggtt tcgccaccgt   1080
ggcgcaagct gaggttcagc tggtcgagtc tggaggcggg cttgtccagc ctggagggag   1140
cctgcgtctc tcttgtgcag caagcggctt cacctttcc tcttacggta tgtcctgggt   1200
gcggcaggca cctgggaagg gcctggagtg gtggcaacc attcgtccg gaggcagcta    1260 tacatactac gtggacagcg tcaagggccg tttcaccatt tcccgggaca atgcaaagaa   1320
taccctttac ctccagatga actctctccg cgcagaggac acagcagtct attactgtgt   1380
acggatcggc gaagacgcgt tggactactg gggacagggg accccttgtga cagtctcctc   1440 tgcttctaca aagggcccat cggtcttccc cctggcaccc cctccaagag cacctctgg    1500 gggcacagcg gccctgggct gcctggtcaa ggactacttc cccgaaccgg tgacggtgtc    1560
gtggaactca ggcgccctga ccagcggcgt gcacaccttc ccggctgtcc tacagtcctc    1620
aggactctac tccctcagca gcgtggtgac cgtgccctcc agcagcttgg gcacccagac   1680
ctacatctgc aacgtgaatc acaagcccag caacaccaag gtcgacaaga agttgagcc    1740 caaatcttgt gacaaaactc acacatgcgc gcgtgatga ggatccaagc ttgcggccgc   1800
gaattcactg gccgtcgttt tacaacgtcg tgactgggaa acctggcg ttacccaact    1860 taatcgcctt gcagcacatc cccctttcgc cagctcgcgt aatagcgaag aggcccgcac   1920
cgatcgccct tcccaacagt tgcgcagcct gaatggcgaa tggcgcctga tgcggtattt   1980
tctccttacg catctgtgcg                                                2000
```

<210> SEQ ID NO 57
<211> LENGTH: 444
<212> TYPE: PRT
<213> ORGANISM: Artificial Sequence
<220> FEATURE:
<223> OTHER INFORMATION: Protein sequence of gH3-grafted heavy chain

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ser Tyr Thr Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

```
Val Arg Ile Gly Glu Asp Ala Leu Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 58
<211> LENGTH: 142
<212> TYPE: PRT
<213> ORGANISM: Artificial Sequence
<220> FEATURE:
<223> OTHER INFORMATION: Amino acid sequence encoded by SEQ ID NO:23

<400> SEQUENCE: 58

Met Lys Met Trp Leu Asn Trp Val Phe Leu Ala Leu Ile Leu Lys Gly
1               5                   10                  15
```

```
Val Gln Cys Glu Val Gln Leu Val Glu Ser Gly Gly Leu Val Gln
             20                  25                  30

Pro Gly Ser Leu Arg Leu Ser Cys Ala Ala Ser Gly Phe Thr Phe
         35                  40                  45

Ser Ser Tyr Gly Met Ser Trp Val Arg Gln Ala Pro Gly Lys Gly Leu
     50                  55                  60

Glu Trp Val Ala Thr Ile Thr Ser Gly Gly Ser Tyr Thr Tyr Tyr Pro
65                  70                  75                  80

Asp Thr Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Ile Gly Glu Asp Ala Leu Asp Tyr Trp Gly Gln
        115                 120                 125

Gly Thr Leu Val Thr Val Ser Ser Ala Ser Thr Lys Gly Pro
    130                 135                 140

<210> SEQ ID NO 59
<211> LENGTH: 129
<212> TYPE: PRT
<213> ORGANISM: Artificial Sequence
<220> FEATURE:
<223> OTHER INFORMATION: Amino acid sequence encoded by SEQ ID NO:24

<400> SEQUENCE: 59

Met Arg Thr Pro Ala Gln Ile Leu Gly Phe Leu Leu Leu Leu Phe Pro
1               5                   10                  15

Gly Thr Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Gln Asp
         35                  40                  45

Ile Ala Gly Ser Leu Asn Trp Tyr Gln Gln Lys Pro Gly Lys Ala Pro
     50                  55                  60

Lys Arg Leu Ile Tyr Ala Thr Ser Ser Leu Asp Ser Gly Val Pro Ser
65                  70                  75                  80

Arg Phe Ser Gly Ser Gly Ser Gly Thr Glu Phe Thr Leu Thr Ile Ser
                 85                  90                  95

Ser Leu Gln Pro Glu Asp Phe Ala Thr Tyr Tyr Cys Leu Gln Tyr Gly
            100                 105                 110

Ser Phe Pro Pro Thr Phe Gly Gln Gly Thr Lys Val Glu Ile Lys Arg
        115                 120                 125

Thr

<210> SEQ ID NO 60
<211> LENGTH: 34
<212> TYPE: PRT
<213> ORGANISM: Artificial Sequence
<220> FEATURE:
<223> OTHER INFORMATION: Amino acid sequence encoded by SEQ ID NO:41

<400> SEQUENCE: 60

Ser Arg Asp Asn Ala Lys Asn Thr Leu Tyr Leu Gln Met Asn Ser Leu
1               5                   10                  15

Arg Ala Glu Asp Thr Ala Val Tyr Tyr Cys Val Arg Ile Gly Glu Asp
             20                  25                  30

Ala Leu
```

<210> SEQ ID NO 61
<211> LENGTH: 21
<212> TYPE: PRT
<213> ORGANISM: Artificial Sequence
<220> FEATURE:
<223> OTHER INFORMATION: Amino acid sequence encoded by SEQ ID NO:42

<400> SEQUENCE: 61

Ser Gly Gly Ser Tyr Thr Tyr Tyr Val Asp Ser Val Lys Gly Arg Phe
1               5                   10                  15

Thr Ile Ser Arg Asp
            20

<210> SEQ ID NO 62
<211> LENGTH: 30
<212> TYPE: PRT
<213> ORGANISM: Artificial Sequence
<220> FEATURE:
<223> OTHER INFORMATION: Amino acid sequence encoded by SEQ ID NO:43

<400> SEQUENCE: 62

Ala Thr Ser Ser Leu Asp Ser Gly Val Pro Lys Arg Phe Ser Gly Ser
1               5                   10                  15

Arg Ser Gly Ser Asp Tyr Thr Leu Thr Ile Ser Ser Leu Gln
            20                  25                  30

<210> SEQ ID NO 63
<211> LENGTH: 37
<212> TYPE: PRT
<213> ORGANISM: Artificial Sequence
<220> FEATURE:
<223> OTHER INFORMATION: Amino acid sequence encoded by SEQ ID NO:44

<400> SEQUENCE: 63

Gly Asp Arg Val Thr Ile Thr Cys Arg Ala Ser Gln Asp Ile Ala Gly
1               5                   10                  15

Ser Leu Asn Trp Leu Gln Gln Lys Pro Gly Lys Ala Ile Lys Arg Leu
            20                  25                  30

Ile Tyr Ala Thr Ser
        35

<210> SEQ ID NO 64
<211> LENGTH: 13
<212> TYPE: PRT
<213> ORGANISM: Artificial Sequence
<220> FEATURE:
<223> OTHER INFORMATION: Amino acid sequence encoded by SEQ ID NO:53

<400> SEQUENCE: 64

Ser Ser Pro Val Thr Lys Ser Phe Asn Arg Gly Glu Cys
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Amino acid sequence encoded by SEQ ID NO:53

<400> SEQUENCE: 65

Met Lys Lys Thr Ala Ile Ala Ile
1               5

<210> SEQ ID NO 66
<211> LENGTH: 13

```
<212> TYPE: PRT
<213> ORGANISM: Artificial Sequence
<220> FEATURE:
<223> OTHER INFORMATION: Amino acid sequence encoded by SEQ ID NO:54

<400> SEQUENCE: 66

Ser Ser Pro Val Thr Lys Ser Phe Asn Arg Gly Glu Cys
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Amino acid sequence encoded by SEQ ID NO:54

<400> SEQUENCE: 67

Met Lys Lys Thr Ala Ile Ala Ile
1               5

<210> SEQ ID NO 68
<211> LENGTH: 13
<212> TYPE: PRT
<213> ORGANISM: Artificial Sequence
<220> FEATURE:
<223> OTHER INFORMATION: Amino acid sequence encoded by SEQ ID NO:55

<400> SEQUENCE: 68

Ser Ser Pro Val Thr Lys Ser Phe Asn Arg Gly Glu Cys
1               5                   10

<210> SEQ ID NO 69
<211> LENGTH: 8
<212> TYPE: PRT
<213> ORGANISM: Artificial Sequence
<220> FEATURE:
<223> OTHER INFORMATION: Amino acid sequence encoded by SEQ ID NO:55

<400> SEQUENCE: 69

Met Lys Lys Thr Ala Ile Ala Ile
1               5

<210> SEQ ID NO 70
<211> LENGTH: 235
<212> TYPE: PRT
<213> ORGANISM: Artificial Sequence
<220> FEATURE:
<223> OTHER INFORMATION: Amino acid sequence encoded by SEQ ID NO:56

<400> SEQUENCE: 70

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Asp Ile Ala Gly Ser Leu Asn Trp Leu Gln Lys Pro Gly Lys Ala
        50                  55                  60

Ile Lys Arg Leu Ile Tyr Ala Thr Ser Ser Leu Asp Ser Gly Val Pro
65                  70                  75                  80

Lys Arg Phe Ser Gly Ser Arg Ser Gly Ser Asp Tyr Thr Leu Thr Ile
                85                  90                  95

Ser Ser Leu Gln Pro Glu Asp Phe Ala Thr Tyr Tyr Cys Leu Gln Tyr
                100                 105                 110
```

```
Gly Ser Phe Pro Pro Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 71
<211> LENGTH: 249
<212> TYPE: PRT
<213> ORGANISM: Artificial Sequence
<220> FEATURE:
<223> OTHER INFORMATION: Amino acid sequence encoded by SEQ ID NO:56

<400> SEQUENCE: 71

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Gly Met Ser Trp Val Arg Gln Ala Pro Gly Lys
    50                  55                  60

Gly Leu Glu Trp Val Ala Thr Ile Thr Ser Gly Gly Ser Tyr Thr Tyr
65                  70                  75                  80

Tyr Val Asp Ser Val Lys Gly Arg Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Val Arg Ile Gly Glu Asp Ala Leu Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205
```

```
                                   -continued
Val Pro Ser Ser Ser Leu Gly Thr Gln Thr Tyr Ile Cys Asn Val Asn
    210             215             220

His Lys Pro Ser Asn Thr Lys Val Asp Lys Lys Val Glu Pro Lys Ser
225             230             235             240

Cys Asp Lys Thr His Thr Cys Ala Ala
                245
```

The invention claimed is:

1. A DNA sequence which encodes the heavy and/or light chain of an antibody molecule having specificity for human KDR, comprising:
   a) a heavy chain wherein the variable domain comprises a CDR having the sequence given in SEQ ID NO:1 for CDRH1, SEQ ID NO:2 or residues 50-66 of SEQ ID NO: 15 for CDRH2 or SEQ ID NO:3 for CDRH3 and a light chain wherein the variable domain comprises a CDR having the sequence given in SEQ ID NO:4 for CDRL1, SEQ ID NO:5 for CDRL2 or SEQ ID NO:6 for CDRL3; or
   b) a heavy chain wherein the variable domain comprises a CDR having the sequence given in SEQ ID NO:1 for CDRH1, SEQ ID NO:2 or residues 50-66 of SEQ ID NO: 15 for CDRH2 and SEQ ID NO:3 for CDRH3 and a light chain wherein the variable domain comprises a CDR having the sequence given in SEQ ID NO:4 for CDRL1, SEQ ID NO:5 for CDRL2 and SEQ ID NO:6 for CDRL3; or
   c) the heavy chain variable region gH3 (SEQ ID NO: 15) and light chain variable region gL3 (SEQ ID NO: 16).

2. A cloning or expression vector containing the DNA sequence of claim 1.

3. An *E. coli* expression vector comprising the DNA sequence of claim 1.

4. The *E. coli* expression vector of claim 3 which is pTTOD (CDP791).

5. A host cell transformed with the vector of claim 2.

6. A DNA sequence which encodes the heavy and/or light chain of an antibody molecule having specificity for human KDR, comprising:
   a light chain comprising the sequence given in amino acids 22 to 235 of SEQ ID NO:11 and a heavy chain comprising the sequence given in SEQ ID NO:57.

7. The DNA sequence of claim 1 or 6 which encodes the heavy and/or light chain of an antibody molecule having specificity for human KDR, wherein the human acceptor framework regions of the variable domain of the heavy chain are
   a) based on a human germline group 3 framework sequence and comprise non-human donor residues at positions 77 and 93; or
   b) based on human germline group 1 framework sequence and comprise non-human donor residues at positions 36, 44, 60, 66, 69, 70 and 71.

8. A cloning or expression vector containing the DNA sequence of claim 6 or 7.

9. An *E. coli* expression vector comprising the DNA sequence of claim 6 or 7.

10. The *E. coli* expression vector of claim 9 which is pTTOD(CDP791).

11. A host cell transformed with the vector of 8.

* * * * *